US012779020B2

(12) United States Patent
Ryu et al.

(10) Patent No.: US 12,779,020 B2
(45) Date of Patent: Nov. 3, 2026

(54) STABILIZED ACE2 VARIANT, ACE2-FC FUSION PROTEIN USING SAME, AND METHOD FOR PREVENTING OR TREATING COVID-19

(71) Applicant: IUCF-HYU (INDUSTRY-UNIVERSITY COOPERATION FOUNDATION HANYANG UNIVERSITY), Seoul (KR)

(72) Inventors: Seong Eon Ryu, Seoul (KR); Myeong Bin Kim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 718 days.

(21) Appl. No.: 18/295,822

(22) Filed: Apr. 4, 2023

(65) Prior Publication Data

US 2023/0293648 A1 Sep. 21, 2023

Related U.S. Application Data

(63) Continuation-in-part of application No. PCT/KR2021/013511, filed on Oct. 1, 2021.

(30) Foreign Application Priority Data

Oct. 5, 2020 (KR) ........................ 10-2020-0128402
Sep. 30, 2021 (KR) ........................ 10-2021-0129658

(51) Int. Cl.

| | |
|---|---|
| ***A61K 38/48*** | (2006.01) |
| ***A61K 39/00*** | (2006.01) |
| ***A61P 31/14*** | (2006.01) |
| ***C07K 16/104*** | (2026.01) |
| ***C07K 16/28*** | (2006.01) |
| ***C12N 9/48*** | (2006.01) |

(52) U.S. Cl.

CPC .......... *A61K 38/4813* (2013.01); *A61K 39/00* (2013.01); *A61P 31/14* (2018.01); *C07K 16/104* (2026.01); *C07K 16/28* (2013.01); *C12N 9/485* (2013.01); *C12Y 304/17023* (2013.01); *C07K 2317/31* (2013.01); *C07K 2319/30* (2013.01)

(58) Field of Classification Search

None

See application file for complete search history.

(56) References Cited

U.S. PATENT DOCUMENTS 6,989,363 B1 1/2006 Acton et al.
2020/0181594 A1 6/2020 Batlle et al.
2021/0371841 A1* 12/2021 Batlle .................... C12N 9/485
2023/0183668 A1* 6/2023 Bailey ................ A61K 38/4813 424/94.3

FOREIGN PATENT DOCUMENTS

KR 10-2015-0110607 A 10/2015
KR 102145197 B1 8/2020
KR 102205028 B1 1/2021
WO 2014/108530 A1 7/2014

OTHER PUBLICATIONS

Procko et al., BioRxiv: 1-21 (Year: 2020).*
Hati, S. et al., "Impact of Thiol-Disulfide Balance on the Binding of Covid-19 Spike Protein with Angiotensin-Converting Enzyme 2 Receptor," ACS Omega, vol. 5, Issue 26, pp. 16292-16298 (Jun. 23, 2020).
Guo, X. et al., "Investigation of the genetic variation in ACE2 on the structural recognition by the novel coronavirus (SARS-CoV-2)," Journal of Translational Medicine, vol. 18, Issue 321, pp. 1-9 (Aug. 24, 2020).
ISR and Written Opinion of PCT application No. PCT/KR2021/013511 mailed Dec. 24, 2021.
Shang et al. "Structural basis of receptor recognition by SARS-CoV-2" Nature | vol. 581 | May 14, 2020.
Fabozzi et al. "Bispecific antibodies: potential immunotherapies for HIV treatment." Methods. Feb. 1, 2019; 154: 118-124. doi:10.1016/j.ymeth.2018.10.010.
Brey et al. "A gB/CD3 bispecific BiTE antibody construct for targeting Human Cytomegalovirus-infected cells" Sci Rep 8, 17453 (Nov. 2018).

* cited by examiner

*Primary Examiner* — Phuong Huynh
(74) *Attorney, Agent, or Firm* — Maschoff Brennan

(57) ABSTRACT

A stabilized Ace2 variant has a disulfide bond introduced by substituting cysteine for amino acid residue pairs at specific positions of the Ace2 protein, thereby having excellent stability. The stabilized Ace2 variant exhibits high binding affinity for SARS-CoV-2 virus and excellent stability even in an aqueous solution condition. When the stabilized Ace2 variant is applied to a therapeutic agent for COVID-19, which is the SARS-CoV-2 infectious disease, the shelf stability, in-vivo stability, and therapeutic effect of the therapeutic agent may all be improved. In addition, since it uses the amino acid sequence derived from the receptor for SARS-CoV-2, it may effectively work even against various virus mutant strains.

8 Claims, 15 Drawing Sheets

Specification includes a Sequence Listing.

Figure 3J

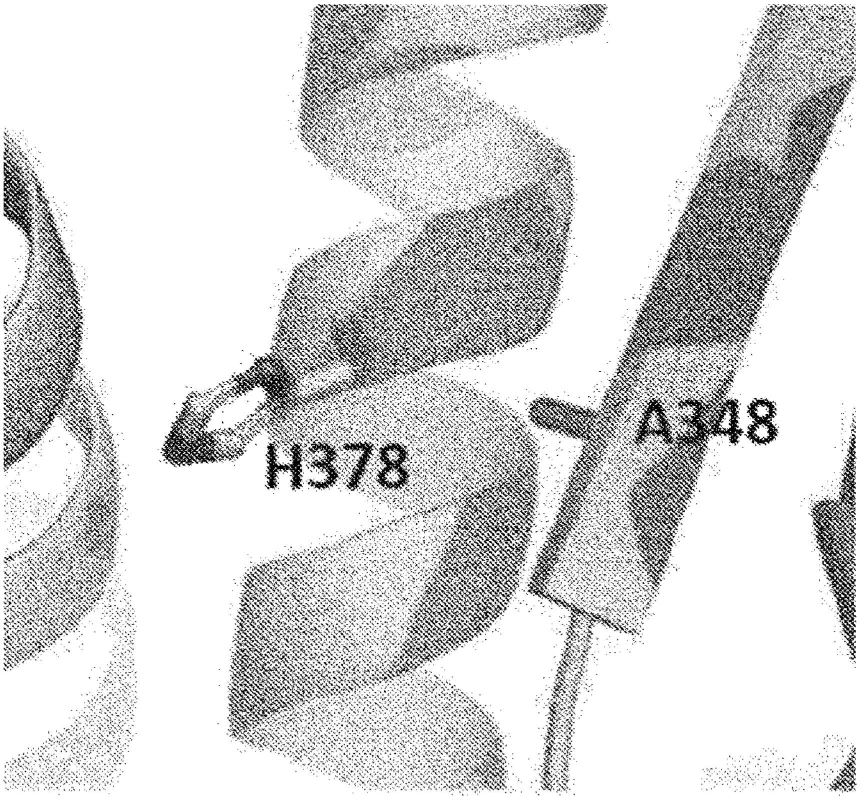

Figure 4A

*

MSSSSWLLLS LVAVTAAQST IEEQAKTFLD KFNHEAEDLF YQSSLASWNY CTNITEENVQ 60

NMNNAGDKWS AFLKEQSTLA QMYPLQEIQN LTVKLQLQAL QQNGSSVLSE DKSKRLNTIL 120

NTMSTIYSTG KVCNPDNPQE CLLLEPGLNE IMANSLDYNE RLWAWESWRS EVGKQLRPLY 180

EEYVVLKNEM ARANHYEDYG DYWRGDYEVN GVDGYDYSRG QLIEDVEHTF EEIKPLYEHL 240

HAYVRAKLMN AYPSYISPIG CLPAHLLGDM WGRFWTNLYS LTVPFGQKPN IDVTDAMVDQ 300

*

AWDAQRIFKE AEKFFVSVGL PNMTQGFWEN SMLTDPGNVQ KACCHPTAWD LGKGDFRILM 360

CTKVTMDDFL TAHHEMGHIQ YDMAYAAQPF LLRNGANEGF HEAVGEIMSL SAATPKHLKS 420

IGLLSPDFQE DNETEINFLL KQALTIVGTL PFTYMLEKWR WMVFKGEIPK DQWMKKWWEM 480

KREIVGVVEP VPHDETYCDP ASLFHVSNDY SFIRYYTRTL YQFQFQEALC QAAKHEGPLH 540

KCDISNSTEA GQKLFNMLRL GKSEPWTLAL ENVVGAKNMN VRPLLNYFEP LFTWLKDQNK 600

NSFVGWSTDW SPYADGSGSG SDKTHTCPPC PAPELLGGPS VFLFPPKPKD TLMISRTPEV 660

TCVVVDVSHE DPEVKFNWYV DGVEVHNAKT KPREEQYNST YRVVSVLTVL HQDWLNGKEY 720

KCKVSNKALP APIEKTISKA KGQPREPQVY TLPPSRDELT KNQVSLTCLV KGFYPSDIAV 780

EWESNGQPEN NYKTTPPVLD SDGSFFLYSK LTVDKSRWQQ GNVFSCSVMH EALHNHYTQK 840

SLSLSPGKGT HHHHHH

Figure 4B

```
                                                                 *
MSSSSWLLLS LVAVTAAQST IEEQAKTFLD KFNHEAEDLF YQSSLASWNY NTCITEENVQ     60
NMNNAGDKWS AFLKEQSTLA QMYPLQEIQN LTVKLQLQAL QQNGSSVLSE DKSKRLNTIL    120
NTMSTIYSTG KVCNPDNPQE CLLLEPGLNE IMANSLDYNE RLWAWESWRS EVGKQLRPLY    180
EEYVVLKNEM ARANHYEDYG DYWRGDYEVN GVDGYDYSRG QLIEDVEHTF EEIKPLYEHL    240
HAYVRAKLMN AYPSYISPIG CLPAHLLGDM WGRFWTNLYS LTVPFGQKPN IDVTDAMVDQ    300
                                          *
AWDAQRIFKE AEKFFVSVGL PNMTQGFWEN SMLTDPGNVC KAVCHPTAWD LGKGDFRILM    360
CTKVTMDDFL TAHHEMGHIQ YDMAYAAQPF LLRNGANEGF HEAVGEIMSL SAATPKHLKS    420
IGLLSPDFQE DNETEINFLL KQALTIVGTL PFTYMLEKWR WMVFKGEIPK DQWMKKWWEM    480
KREIVGVVEP VPHDETYCDP ASLFHVSNDY SFIRYYTRTL YQFQFQEALC QAAKHEGPLH    540
KCDISNSTEA GQKLFNMLRL GKSEPWTLAL ENVVGAKNMN VRPLLNYFEP LFTWLKDQNK    600
NSFVGWSTDW SPYADGSGSG SDKTHTCPPC PAPELLGGPS VFLFPPKPKD TLMISRTPEV    660
TCVVVDVSHE DPEVKFNWYV DGVEVHNAKT KPREEQYNST YRVVSVLTVL HQDWLNGKEY    720
KCKVSNKALP APIEKTISKA KGQPREPQVY TLPPSRDELT KNQVSLTCLV KGFYPSDIAV    780
EWESNGQPEN NYKTTPPVLD SDGSFFLYSK LTVDKSRWQQ GNVFSCSVMH EALHNHYTQK    840
SLSLSPGKGT HHHHHH
```

Figure 4C

```
                                                                 *
MSSSSWLLLS LVAVTAAQST IEEQAKTFLD KFNHEAEDLF YQSSLASWNY NTNCTEENVQ     60
NMNNAGDKWS AFLKEQSTLA QMYPLQEIQN LTVKLQLQAL QQNGSSVLSE DKSKRLNTIL    120
NTMSTIYSTG KVCNPDNPQE CLLLEPGLNE IMANSLDYNE RLWAWESWRS EVGKQLRPLY    180
EEYVVLKNEM ARANHYEDYG DYWRGDYEVN GVDGYDYSRG QLIEDVEHTF EEIKPLYEHL    240
HAYVRAKLMN AYPSYISPIG CLPAHLLGDM WGRFWTNLYS LTVPFGQKPN IDVTDAMVDQ    300
                                            *
AWDAQRIFKE AEKFFVSVGL PNMTQGFWEN SMLTDPGNVQ CAVCHPTAWD LGKGDFRILM    360
CTKVTMDDFL TAHHEMGHIQ YDMAYAAQPF LLRNGANEGF HEAVGEIMSL SAATPKHLKS    420
IGLLSPDFQE DNETEINFLL KQALTIVGTL PFTYMLEKWR WMVFKGEIPK DQWMKKWWEM    480
KREIVGVVEP VPHDETYCDP ASLFHVSNDY SFIRYYTRTL YQFQFQEALC QAAKHEGPLH    540
KCDISNSTEA GQKLFNMLRL GKSEPWTLAL ENVVGAKNMN VRPLLNYFEP LFTWLKDQNK    600
NSFVGWSTDW SPYADGSGSG SDKTHTCPPC PAPELLGGPS VFLFPPKPKD TLMISRTPEV    660
TCVVVDVSHE DPEVKFNWYV DGVEVHNAKT KPREEQYNST YRVVSVLTVL HQDWLNGKEY    720
KCKVSNKALP APIEKTISKA KGQPREPQVY TLPPSRDELT KNQVSLTCLV KGFYPSDIAV    780
EWESNGQPEN NYKTTPPVLD SDGSFFLYSK LTVDKSRWQQ GNVFSCSVMH EALHNHYTQK    840
SLSLSPGKGT HHHHHH
```

Figure 4D

```
MSSSSWLLLS LVAVTAAQST IEEQAKTFLD KFNHEAEDLF YQSSLASWNY NTNITEENVQ    60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
                                                            *
EEYVVLKNEM ARANHYEDYG DYWRGDYEVN GVDGYDYSRG QLIEDVEHTF EEIKPLYECL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
   *
NSFCGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4E

```
                     *
MSSSSWLLLS LVAVTAAQST CEEQAKTFLD KFNHEAEDLF YQSSLASWNY NTNITEENVQ    60
                           *
NMNNAGDKWS AFLKEQSTLA QMYPLQCIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4F

```
                                              *
MSSSSWLLLS LVAVTAAQST IEEQAKTFLD KFNHEAEDLF YQSSLACWNY NTNITEENVQ    60
 *
NCNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4G

```
MSSSSWLLLS LVAVTAAQST IEEQAKTFLD KFNHEAEDLF YQSSLASWNY NTNITEENVQ    60
                                                  *
NMNNAGDKWS AFLKEQSTLA QMYPLQEIQN LTVKLQLQAL QQNGSSCLSE DKSKRLNTIL   120
NTMSTIYSTG KVCNPDNPQE CLLLEPGLNE IMANSLDYNE RLWAWESWRS EVGKQLRPLY   180
             *
EEYVVLKNEM ARCNHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4H

MSSSSWLLLS LVAVTAAQST IEEQAKTFLD KFNHEAEDLF YQSSLASWNY NTNITEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVTDAMCDQ 300
AWDAQRIFKE AEKFFVSVGL PNMTQGFWEN SMLTDPGNVQ KAVCHPTAWD LGKGDFRILM 360
CTKCTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYADGSGSG SDKTHTCPPC PAPELLGGPS VFLFPPKPKD TLMISRTPEV 660
TCVVVDVSHE DPEVKFNWYV DGVEVHNAKT KPREEQYNST YRVVSVLTVL HQDWLNGKEY 720
KCKVSNKALP APIEKTISKA KGQPREPQVY TLPPSRDELT KNQVSLTCLV KGFYPSDIAV 780
EWESNGQPEN NYKTTPPVLD SDGSFFLYSK LTVDKSRWQQ GNVFSCSVMH EALHNHYTQK 840
SLSLSPGKGT HHHHHH

Figure 4I

MSSSSWLLLS LVAVTAAQST IEEQAKTFLD KFNHEAEDLF YQSSLASWNY NTNITEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVCDAMVDQ 300
AWDAQRIFKE AEKFFVSVGL PNMTQGFWEN SMLTDPGNVQ KAVCHPTAWD LGKGDFRILM 360
CTKVCMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYADGSGSG SDKTHTCPPC PAPELLGGPS VFLFPPKPKD TLMISRTPEV 660
TCVVVDVSHE DPEVKFNWYV DGVEVHNAKT KPREEQYNST YRVVSVLTVL HQDWLNGKEY 720
KCKVSNKALP APIEKTISKA KGQPREPQVY TLPPSRDELT KNQVSLTCLV KGFYPSDIAV 780
EWESNGQPEN NYKTTPPVLD SDGSFFLYSK LTVDKSRWQQ GNVFSCSVMH EALHNHYTQK 840
SLSLSPGKGT HHHHHH

Figure 4J

```
MSSSSWLLLS LVAVTAAQST IEEQAKTFLD KFNHEAEDLF YQSSLASWNY NTNITEENVQ    60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGCIQ YDMAYAAQPF LLRNGANEGF CEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4K

```
MSSSSWLLLS LVAVTAAQST IEEQAKTFLD KFNHEAEDLF YQSSLASWNY NTNITEENVQ    60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWCNLYS LTVPFGQKPN IDVTDAMVDQ   300
AWDAQRIFKE AEKFFVSVGL PNMTQGFWEN SMLTDPGNVQ KAVCHPTAWD LGKGDFRILM   360
CTKVTMDDFL TAHHEMGHIQ YDMAYAAQPF LLRNGANEGF HEAVGEIMSL SAATPKHLKS   420
IGLLSPDFQE DNETEINFLL KQALCIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 4L

```
MSSSSWLLLS LVAVTAAQST IEEQAKTFLD KFNHEAEDLF YQSSLASWNY NTNITEENVQ   60
NMNNAGDKWS AFLKEQSTLA QMYPLQEIQN LTVKLQLQAL QQNGSSVLSE DKSKRLNTIL  120
                                                     *
NTMSTIYSTG KVCNPDNPQE CLLLEPGLNE IMANSLDYNE RLWAWESWQS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
                       *
KREIVGVVEP VPHDETYCDP ACLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADGSGSG SDKTHTCPPC PAPELLGGPS VFLFPPKPKD TLMISRTPEV  660
TCVVVDVSHE DPEVKFNWYV DGVEVHNAKT KPREEQYNST YRVVSVLTVL HQDWLNGKEY  720
KCKVSNKALP APIEKTISKA KGQPREPQVY TLPPSRDELT KNQVSLTCLV KGFYPSDIAV  780
EWESNGQPEN NYKTTPPVLD SDGSFFLYSK LTVDKSRWQQ GNVFSCSVMH EALHNHYTQK  840
SLSLSPGKGT HHHHHH
```

Figure 4M

```
MSSSSWLLLS LVAVTAAQST IEEQAKTFLD KFNHEAEDLF YQSSLASWNY NTNITEENVQ   60
NMNNAGDKWS AFLKEQSTLA QMYPLQEIQN LTVKLQLQAL QQNGSSVLSE DKSKRLNTIL  120
   *
NTMCTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
                              *
KREIVGVVEP VPHDETYCDP ASLFHVSCDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADGSGSG SDKTHTCPPC PAPELLGGPS VFLFPPKPKD TLMISRTPEV  660
TCVVVDVSHE DPEVKFNWYV DGVEVHNAKT KPREEQYNST YRVVSVLTVL HQDWLNGKEY  720
KCKVSNKALP APIEKTISKA KGQPREPQVY TLPPSRDELT KNQVSLTCLV KGFYPSDIAV  780
EWESNGQPEN NYKTTPPVLD SDGSFFLYSK LTVDKSRWQQ GNVFSCSVMH EALHNHYTQK  840
SLSLSPGKGT HHHHHH
```

Figure 4N

```
MSSSSWLLLS LVAVTAAQST IEEQAKTFLD KFNHEAEDLF YQSSLASWNY NTNITEENVQ    60
NMNNAGDKWS AFLKEQSTLA QMYPLQEIQN LTVKLQLQAL QQNGSSVLSE DKSKRLNTIL   120
NTMSTIYSTG KVCNPDNPQE CLLLEPGLNE IMANSLDYNE RLWAWESWRS EVGKQLRPLY   180
EEYVVLKNEM ARANHYEDYG DYWRGDYEVN GVDGYDYSRG QLIEDVEHTF EEIKPLYEHL   240
HAYVRAKLMN AYPSYISPIG CLPAHLLGDM WGRFWTNLYS LTVPFGQKPN IDVTDAMVDQ   300
AWDAQRIFKE AEKFFVSVGL PNMTQGFWEN SMLTDPGNVQ KAVCHPTCWD LGKGDFRILM   360
CTKVTMDDFL TAHHEMGCIQ YDMAYAAQPF LLRNGANEGF HEAVGEIMSL SAATPKHLKS   420
IGLLSPDFQE DNETEINFLL KQALTIVGTL PFTYMLEKWR WMVFKGEIPK DQWMKKWWEM   480
KREIVGVVEP VPHDETYCDP ASLFHVSNDY SFIRYYTRTL YQFQFQEALC QAAKHEGPLH   540
KCDISNSTEA GQKLFNMLRL GKSEPWTLAL ENVVGAKNMN VRPLLNYFEP LFTWLKDQNK   600
NSFVGWSTDW SPYADGSGSG SDKTHTCPPC PAPELLGGPS VFLFPPKPKD TLMISRTPEV   660
TCVVVDVSHE DPEVKFNWYV DGVEVHNAKT KPREEQYNST YRVVSVLTVL HQDWLNGKEY   720
KCKVSNKALP APIEKTISKA KGQPREPQVY TLPPSRDELT KNQVSLTCLV KGFYPSDIAV   780
EWESNGQPEN NYKTTPPVLD SDGSFFLYSK LTVDKSRWQQ GNVFSCSVMH EALHNHYTQK   840
SLSLSPGKGT HHHHHH
```

Figure 5

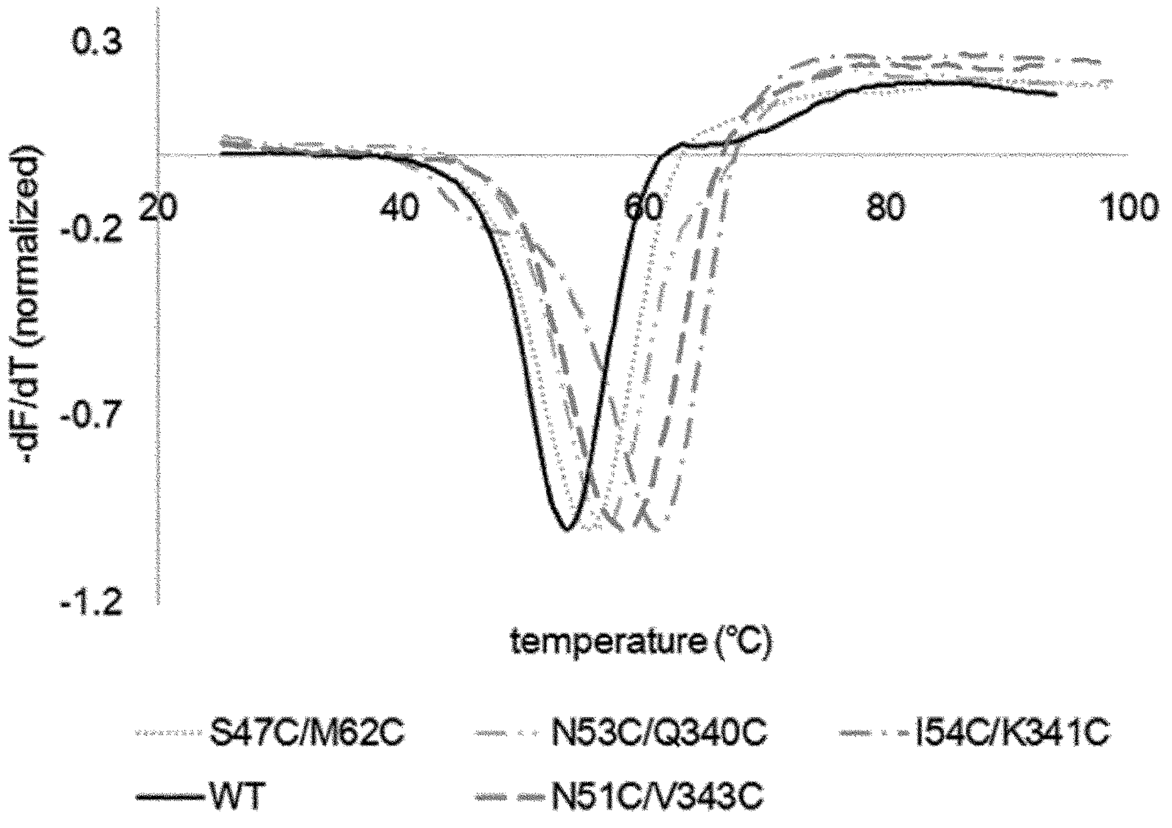

STABILIZED ACE2 VARIANT, ACE2-FC FUSION PROTEIN USING SAME, AND METHOD FOR PREVENTING OR TREATING COVID-19

CROSS-REFERENCE TO RELATED APPLICATIONS

This application is a continuation-in-part application of International Patent Application No. PCT/KR2021/013511 filed on Oct. 1, 2021, and designating the U.S., which is based upon and claims priority under Korean Patent Application No. 10-2020-0128402 filed Oct. 5, 2020, and Korean Patent Application No. 10-2021-0129658 filed Sep. 30, 2021, the entire contents of which are incorporated herein by reference.

REFERENCE TO AN ELECTRONIC SEQUENCE LISTING

The contents of the electronic sequence listing (Sequence-Listing.xml; Size: 24,000 bytes; and Date of Creation: Mar. 31, 2023) is herein incorporated by reference in its entirety.

TECHNICAL FIELD

The present invention relates to a stabilized Ace2 variant, an Ace2-Fc fusion protein using the same, and a method for preventing or treating COVID-19, and more specifically, to an Ace2 variant having enhanced stability through a disulfide bond, an Ace2-Fc fusion protein using the same, and a method for preventing or treating COVID-19.

BACKGROUND ART

Coronavirus infectious disease-19 (COVID-19) has spread rapidly since its outbreak in December 2019, and the World Health Organization (WHO) has declared COVID-19 a global pandemic following Hong Kong flu and swine flu.

The pathogen of COVID-19 is SARS-CoV-2, is transmitted when droplets from an infected person penetrate the respiratory tract or mucous membranes of the eyes, nose, and mouth, and may show symptoms such as fever and respiratory symptoms such as cough or shortness of breath, and pneumonia, after a latent period of about 2 to 14 days. COVID-19 is highly contagious and may be fatal and lead to death in severe cases, if infected to people with low immune function, such as the elderly or those with underlying diseases. In addition, with the rapid spread of COVID-19, damage is occurring not only in the health sector but also in various areas such as society and the economy. Thus, the development of vaccines and therapeutic agents for COVID-19 is urgently needed.

As an example of a therapeutic agent for COVID-19, antiviral agents using nucleoside analogues are being developed. For example, Korean Patent No. 10-2145197 describes the use of a drug comprising a specific L-nucleoside compound for treating coronavirus infection. However, currently approved antiviral agents have been found to be effective only in very severely ill patients.

Another type of therapeutic agent is a therapeutic agent using an antibody. An antibody therapeutic agent is a therapeutic agent with a mechanism in which an antibody injected from the outside binds to the spike protein on the surface of the virus to prevent the virus from invading human cells. For example, Korean Patent No. 10-2205028 describes various antibody therapeutic agents that bind to the spike protein on the surface of SARS-CoV-2 to neutralize the virus.

In the case of SARS-CoV-2, a number of virus mutant strains have been reported since the virus was first discovered, and in particular, mutant strains such as B.1.1.7 and B.1.351 were found to be more contagious than existing viruses. However, since antibodies bind only to specific antigens, there was a problem that antibody therapeutic agents against SARS-CoV-2 and its virus mutant strains could not work properly against strains other than the target virus.

Thus, there is a need to develop a therapeutic agent that may have a strong therapeutic effect on SARS-CoV-2 virus infectious diseases and also exhibit the effect against various virus mutant strains.

The present inventors found that the use of Ace2-derived protein, which is a receptor that induces human cell infection of SARS-CoV-2, may effectively prevent the virus from invading human cells due to the high binding affinity between the spike protein on the surface of SARS-CoV-2 and the Ace2 protein.

However, there is a problem that the wild-type Ace2 protein has a fluidity in which a part of the structure moves when interacting with angiotensin peptide, so its stability is not high. Wild-type Ace2 in the cell membrane protein state may be stabilized through interaction with angiotensin peptide and interaction with other proteins and biomolecules in the cell membrane, but its stability may be very low in the soluble Ace2 state, so there was a limitation that it was difficult to apply to a therapeutic agent.

Accordingly, in order to develop a therapeutic agent with excellent therapeutic effect using the Ace2 protein, there is a need to solve the stability problem of the Ace2 protein.

DISCLOSURE

Technical Problem

It is an object of the present invention to provide a stabilized Ace2 variant through a disulfide bond.

It is another object of the present invention to provide an Ace2-Fc fusion protein using the stabilized Ace2 variant.

It is another object of the present invention to provide a method for preventing or treating COVID-19 using the stabilized Ace2 variant.

Technical Solution

In order to achieve the above objects, the present invention provides a stabilized angiotensin-converting enzyme 2 (Ace2) variant comprising a disulfide bond formed by substituting cysteine for one or more of the amino acid residue pairs present in an Ace2-derived protein.

In the present invention, the distance between the central carbons (C-alphas) in the amino acid residue pairs forming the disulfide bond is preferably from 4.5 to 7.0 Å.

In the present invention, the amino acid residue pairs may comprise one or more selected from the group consisting of N51/V343, N53/Q340, 154/1(341, H239/V604, 121/E87, M62/S47, A193/V107, V364/V298, T365/T294, H401/H378, T445/T276, S502/R169, N508/S124 and A348/H378, present in the Ace2-derived protein.

In the present invention, the Ace2-derived protein may be a protein derived from an ectodomain of an Ace2 protein.

In the present invention, the Ace2-derived protein may comprise residues at positions 1 to 615 of a wild-type Ace2 protein.

The present invention also provides an Ace2-Fc fusion protein comprising the stabilized Ace2 variant linked to one or more of two chains constituting an immunoglobulin (Ig)-derived Fc domain.

In the present invention, the stabilized Ace2 variant and the Fc domain may be linked through a linker consisting of 0 to 20 amino acid residues.

In the present invention, the Ace2-Fc fusion protein may be a homodimer or a heterodimer. In the present invention, the immunoglobulin may be IgG1, IgG2, IgG3, or IgG4.

In the present invention, the chains constituting the Fc domain may comprise amino acid residues at positions 221 to 447 (based on EU numbering) of the heavy chain of an IgG1.

In the present invention, one or more amino acids in one chain of the Fc domain may be substituted with an amino acid selected from the group consisting of tryptophan (W), arginine (R), phenylalanine (F), and tyrosine (Y); and one or more amino acids in the other chain may be substituted with an amino acid selected from the group consisting of alanine (A), serine (S), threonine (T), and valine (V).

In the present invention, the Ace2-Fc fusion protein may be a bispecific or multispecific antibody further comprising a protein that binds to an antigen on the surface of an immune cell.

In the present invention, the immune cell may be a natural killer cell (NK cell) or T cell.

The present invention also provides a pharmaceutical composition for preventing or treating coronavirus infectious disease 19 (COVID-19), comprising the Ace2-Fc fusion protein.

The present invention also provides a method of preventing or treating COVID-19, comprising administering a pharmaceutical composition comprising the Ace2-Fc fusion protein.

Advantageous Effects

According to the present invention, by substituting cysteine for the residue pairs at specific positions of the Ace2 protein to introduce a disulfide bond, there may be provided an Ace2 protein variant which is of high binding affinity for SARS-CoV-2 virus and exhibits excellent stability even in an aqueous solution condition. Accordingly, when the stabilized Ace2 variant of the present invention is applied to a therapeutic agent for COVID-19, which is the SARS-CoV-2 infectious disease, the shelf stability, in-vivo stability, and therapeutic effect may all be improved. In addition, since it uses the amino acid sequence derived from the receptor for SARS-CoV-2, it may effectively work even against various virus mutant strains.

DESCRIPTION OF DRAWINGS

FIGS. 3A to 3J show the positions of residue pairs to be mutated for helix-helix stabilization (3A to 3I) and the position of residue pair to be mutated for strand-helix stabilization (3J) according to an embodiment of the present invention in the three-dimensional structure of Ace2 protein.

FIGS. 4A to 4N show amino acid sequences (Ace2 variant-linker-Fc region-tag) encoded by the expression vector of the stabilized Ace2-Fc fusion protein according to an embodiment of the present invention. In FIGS. 4A to 4N, the amino acid sequences of each Ace2 variant correspond to SEQ ID NO: 3 to 16, respectively.

FIG. 5 shows first derivative melting curves of the stabilized Ace2-Fc fusion protein according to an embodiment of the present invention and a wild-type Ace2-Fc fusion protein.

BEST MODE

Unless defined otherwise, all technical and scientific terms used in the present specification have the same meaning as commonly understood by those of ordinary skill in the technical field to which the present invention pertains. In general, the nomenclature used in the present specification is those well known and commonly used in the art.

The present invention relates to a stabilized Ace2 variant through a disulfide bond.

Ace2 is an abbreviation of angiotensin-converting enzyme 2 and is a carboxypeptidase related to angiotensin-converting enzyme (ACE). Ace2 is a functional receptor for the coronavirus associated with severe acute respiratory syndrome (SARS), and when SARS-CoV-2 invades the human body, Ace2 binds to the spike protein of SARS-CoV-2 to result in infection.

Ace2 protein consists of 805 amino acids, and is divided into an ectodomain, a membrane spanning domain, and a cytoplasmic domain. Among them, the ectodomain of the Ace2 protein is a soluble protein consisting of about 600 amino acids and has high affinity with the spike protein of the SARS-CoV-2 virus. The present inventors found that the interaction and infection of the SARS-CoV-2 virus and target cells may be prevented by using the property that the protein derived from the ectodomain of Ace2 binds strongly to the spike protein of SARS-CoV-2 in this way.

However, it is known that the ectodomain of Ace2 protein has a fluidity in which a part of the protein structure moves when interacting with angiotensin peptide for its natural function, so its stability is not high. Wild-type Ace2 in the cell membrane protein state may be stabilized through interaction with angiotensin peptide and interaction with other proteins and biomolecules in the cell membrane, but its stability is very low in the soluble Ace2 state, so there was a problem that it was difficult to apply to a therapeutic agent.

Figure 1:
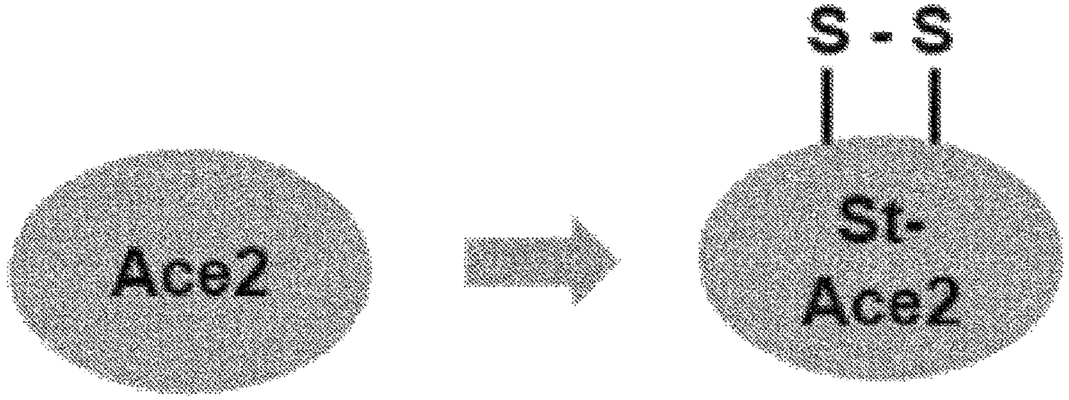
FIG. 1 shows a schematic design of the stabilized Ace2 variant provided in the present invention.

The present invention is to solve the problem of instability of the Ace2 protein, and the stabilized Ace2 variant of the present invention is one in which a mutation is formed to introduce a disulfide bond into the Ace2-derived protein, as shown in FIG. 1.

By substituting one or more of the specific amino acid residue pairs of the Ace2 protein with cysteine to form a structurally stable disulfide bond, the present inventors developed a variant capable of maintaining high binding affinity to viruses by minimizing structural modification due to disulfide bond formation while being stable even in the soluble Ace2 state by improving the thermal stability and structural stability of the Ace2 protein.

In the present invention, the term "disulfide bond" refers to a state in which a sulfide (—SH) group in cysteine among protein amino acids meets a sulfide group of another cysteine to form a covalent bond, and provides great stability to the protein structure.

In the present invention, the term "soluble Ace2" refers to one that was made in the form of a protein in a stable state in an aqueous solution, rather than a wild-type membrane protein, after the ectodomain of Ace2 has been cut out by genetic manipulation. As such, a soluble receptor made from a virus receptor may be used to prevent the virus from invading cells.

In the present invention, the term "variation" is meant to include substitutions, insertions and/or deletions of amino acid residues, and preferably, the variants of the present invention include substitutions of amino acid residues. Substitution of an amino acid residue may be represented by the sequence of the residue in the parent amino acid sequence, the position number of the amino acid residue, and the amino acid residue substituted.

In the present invention, the mutation for introducing the disulfide bond may include a variation in which one or more of the amino acid residue pairs present in the Ace2-derived protein is substituted with cysteine. In this case, the amino acid residue pair is a pair of two amino acids consisting of amino acids other than cysteine, and in order to form a disulfide bond through cysteine substitution to effectively stabilize the structure, the distance between the central carbons (C-alphas) of the amino acids forming the residue pair is preferably from 4.5 to 7.0 Å.

In the present invention, the amino acid residue pairs to be mutated may comprise one or more residue pairs selected from the group consisting of N51/V343, N53/Q340, I54/K341, H239/V604, I21/E87, M62/547, A193/V107, V364/V298, T365/T294, H401/H378, T445/T276, 5502/R169, N508/S124 and A348/H378, present in the Ace2-derived protein.

In an embodiment of the present invention, it was confirmed that the residue pairs had the distance between C-alphas within the range of 4.5 to 7.0 Å and were involved in stabilizing the loop region at positions 331-347, loop region at positions 599-614, helix-helix region and strand-helix region of the Ace2 protein, through 3D structure analysis of the Ace2 protein. In addition, experimental results were obtained showing that when a disulfide bond was formed at the amino acid residue pair, the melting temperature of the protein was significantly increased compared to that of the wild type, but the binding force with the virus was hardly affected. Thus, according to the variant of the present invention, it was confirmed that structural distortion was minimized due to disulfide bond formation, so that improved structural stability compared to wild-type Ace2 protein could be realized, and excellent binding affinity with the viruses, which is a characteristic of Ace2, was maintained.

In the present invention, the Ace2-derived protein that is the parent of the mutant may comprise the following amino acid sequence of SEQ ID NO: 1 corresponding to positions 1 to 615 of the Ace2 protein:

```
Positions 1 to 615 of Ace2
                                   [SEQ ID NO: 1]
MSSSSWLLLSLVAVTAAQSTIEEQAKTFLDKFNHEAEDLFYQSSLASWNY

NTNITEENVQNMNNAGDKWSAFLKEQSTLAQMYPLQEIQNLTVKLQLQAL

QQNGSSVLSEDKSKRLNTILNTMSTIYSTGKVCNPDNPQECLLLEPGLNE
```

-continued

```
IMANSLDYNERLWAWESWRSEVGKQLRPLYEEYVVLKNEMARANHYEDYG

DYWRGDYEVNGVDGYDYSRGQLIEDVEHTFEEIKPLYEHLHAYVRAKLMN

AYPSYISPIGCLPAHLLGDMWGRFWTNLYSLTVPFGQKPNIDVTDAMVDQ

AWDAQRIFKEAEKFFVSVGLPNMTQGFWENSMLTDPGNVQKAVCHPTAWD

LGKGDFRILMCTKVTMDDFLTAHHEMGHIQYDMAYAAQPFLLRNGANEGF

HEAVGEIMSLSAATPKHLKSIGLLSPDFQEDNETEINFLLKQALTIVGTL

PFTYMLEKWRWMVFKGEIPKDQWMKKWWEMKREIVGVVEPVPHDETYCDP

ASLFHVSNDYSFIRYYTRTLYQFQFQEALCQAAKHEGPLHKCDISNSTEA

GQKLFNMLRLGKSEPWTLALENVVGAKNMNVRPLLNYFEPLFTWLKDQNK

NSFVGWSTDWSPYAD
```

Specifically, in the Ace2-derived protein, the loop region at positions 331-347, which is a fluid loop of the Ace2 protein, may be stabilized through one or more variations selected from the group consisting of N51C/V343C, N53C/Q340C and I54C/K341C, and the loop region at positions 599-614 may be stabilized through the H239C/V604C variation. In this regard, according to one example of the present invention, the stabilization of Ace2 protein was confirmed from the experiment results that the melting temperature of the fusion proteins prepared using Ace2-derived proteins having N51C/V343C, N53C/Q340C or I54C/K341C variation was higher than that of wild type.

In addition, the helices of the Ace2 protein may be stably linked through one or more variations selected from the group consisting of I21C/E87C, M62C/S47C, A193C/V107C, V364C/V298C, T365C/T294C, H401C/H378C, T445C/T276C, S502C/R169C and N508C/S124C, and the strand and helix may be stably linked through the A348C/H378C variation. In this regard, according to one example of the present invention, the stabilization of Ace2 protein was confirmed from the experiment results that the melting temperature of the fusion protein prepared using Ace2-derived protein having S47C/M62C variation was higher than that of wild type.

In this way, the Ace2 variant stabilized through the formation of a disulfide bond by substituting a target residue pair with cysteine may exhibit excellent therapeutic effects due to its high binding force to the SARS-CoV-2 virus, like wild-type Ace2. In addition, since it is stable even in the soluble Ace2 state, a long-term drug effect may be exhibited even at a low dose by maintaining a structure effective for disease treatment in the human body for a long period of time.

In one embodiment of the present invention, an Ace2-Fc fusion protein may be formed using the stabilized Ace2 variant.

In the present invention, the Ace2-Fc fusion protein refers to a protein constructed by linking a soluble Ace2 protein to an immunoglobulin-derived Fc domain.

In the present invention, the immunoglobulin-derived Fc domain refers to a C-terminal region including CH2 and CH3 domains (or CH2, CH3 and CH4 domains) of a constant region in the heavy chain of an immunoglobulin, and is used as a meaning encompassing the wild-type Fc domain and its variant. The parent immunoglobulin of the Fc domain may be IgG1, IgG2, IgG3, or IgG4, and preferably may be IgG1.

In the present invention, each chain of the Fc domain may include a region extending from residue at position 221 of the heavy chain of a human IgG1 to the C-terminus, or a region further including a hinge in the region. The number of amino acid residues in the Fc region is according to EU numbering (see Kabat et al.), which defines the number of residues in the heavy chains of human immunoglobulins.

In the present invention, each chain of the Fc domain may include the sequence at positions 221 to 447 of the heavy chain of the IgG1. The sequence at positions 221 to 447 of the heavy chain of the IgG1 may be represented by the following amino acid sequence of SEQ ID NO: 2:

```
Positions 221 to 447 of the heavy chain of the
IgG1
                                    [SEQ ID NO: 2]
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK
```

In the Ace2-Fc fusion protein of the present invention, the stabilized Ace2 variant may be linked to one or more of two chains constituting the Fc domain.

In this case, the Ace2 variant and the Fc domain may be linked by 0 to 20 amino acid residues. That is, the Ace2 variant and the Fc domain may be directly linked, or linked through a linker consisting of 1 to 20 amino acids. In addition, the Ace2 variant may be linked to the N-terminus or C-terminus of the Fc domain.

The Ace2-Fc fusion protein of the present invention may be in the form of a homodimer or a heterodimer, and may be in a form in which the Ace2 variant is linked to both chains of the Fc domain or linked to only one chain.

In an embodiment of the present invention, when the Ace2-Fc fusion protein forms a heterodimer, for example, a bispecific (or multispecific) antibody, a recombinant variant for forming a dimer in the Fc domain may be formed.

For example, the recombinant variant for forming a dimer may be formed using a knobs-into-hole technology.

The knob-into-hole technology is a technology designed to form only heterodimers between heavy chains of antibody fragments. In this case, the knob is designed to have a side chain protruding from the opposite chain, and is inserted into a hole of the opposite domain. Due to this, heavy chains cannot be homodimerized by side chain collision, but can only be heterodimerized. In the present invention, a structure in which knobs or holes are formed in each chain of the Fc domain may be referred to as an Fc-knob or an Fc-hole, respectively.

The Fc-knob may be formed by substituting one or more amino acids in the chain constituting the Fc domain with a large amino acid selected from the group consisting of tryptophan (W), arginine (R), phenylalanine (F) and tyrosine (Y). For example, the Fc-knob may have T366W variation formed in the sequences at positions 221 to 447 of the IgG1-Fc heavy chain.

The Fc-hole may be formed by substituting one or more amino acids in the chain constituting the Fc domain with a small amino acid selected from the group consisting of alanine (A), serine (S), threonine (T) and valine (V). For example, the Fc-hole may have T366S, L368A and Y407V variations formed in the sequences at positions 221 to 447 of the IgG1-Fc heavy chain.

In this way, when the stabilized Ace2 variant of the present invention is fused with the Fc domain, the Ace2 variant may not only inhibit infection by strongly binding to the virus, but also remove the virus by inducing an immune response, and enhance the drug effects by extending the retention period in the body through interaction with Fc receptors. In addition, by constructing a bispecific or multispecific antibody using this and inducing a NK cell or an immune cell into an infected cell, virus-derived diseases may be treated through active killing of infected cells and activation of immune responses.

In the present invention, the term "bispecific (or multispecific) antibody" refers to an antibody capable of binding to two (or more) different types of antigens, and includes forms produced by genetic engineering. In the present invention, the bispecific (or multispecific) antibody may refer to an antibody that simultaneously binds to a target antigen and an antigen on the surface of an immune cell to induce killing of the target antigen by antibody-dependent cytotoxicity.

In the present invention, the bispecific (or multispecific) antibody may be in the form of Fab, Fab', F(ab')2, Fv fragment, rIgG, single chain Fv fragment (scFv), tandem single chain Fv fragment (scFv)2, bispecific T-cell engager (BiTE), diabody, tandem diabody (TandAb), triabody, or tetrabody.

In the present invention, the term "immune cell" is a cell that recognizes and directly or indirectly attacks an antigen, and may preferably be a natural killer cell (NK cell) or T cell.

In the present invention, the term "antigen on the surface of an immune cell" is a concept including target molecules and antigens present on the surface of immune cells. For example, the antigen on the surface of an immune cell may be selected from the group consisting of IL-1 alpha, IL-1 beta, IL-1R, IL-4, IL-5, IL-6R, IL-9, IL-12, IL-13, IL-18, IL-18R, IL-25, TARC, MDC, MEF, TGF-β, LHR agonist, TWEAK, CL25, SPRR2a, SPRR2b, ADAMS, PED2, TNF alpha, TGF beta, VEGF, MIF, ICAM-1, PGE4, PEG2, RANK ligand, Te38, BAFF, CTLA-4, GP130, HER1, HER2, HER3, HER4, VEGF-A, PDGF, VEGF-A, VEGF-C, VEGF-D, DR5, MET, EGFR, MAPG, CSPGs, CTLA-4, IGF1, IGF2, Erb2B, MAG, RGM A, NogoA, NgR, OMGp, PDL-I, NRP1, NRP2, 2B4, CD2, CD3 zeta, CD3, CD8, CD16, CD19, CD20, CD22, CD27, CD28, CD40, CD56, CD57, CD62L, CD64, CD94, CD96, CD100, CD160, CD244, CEACAM1, CRACC, CRTAM, CS1, DAP10, DAP12, DNAM-1(CD226), FcR gamma, KIRs (KIR2DS1, KIR2DS2, KIR2DS3, KIR2DS4, KIR2DS5, KIR2DL4, KIR3DL2, KIR3DS1), LFA-1, NCRs, NKG2A, NKG2C, NKG2D, NKG2E, NKG2H, NKp30a, NKp30b, NKp44, NKp46, NKp80, NTB-A, OX40, PSGL1, semaphoring 4D, SLAMF4, SLAMF6, SLAMF7, TIGIT, TLR, and TRAIL. Alternatively, it may also be used in the form of a multispecific antibody that binds to one or more of these additional target molecules.

In the Ace2-Fc fusion protein of the present invention, a bispecific antibody may be constructed by linking a stabilized Ace2 variant and a binding protein that binds to an antigen on the surface of an immune cell to the chains of the Fc domain, respectively. These bispecific antibodies may bind simultaneously to the SARS-CoV-2 virus and antigens on the surface of immune cells. Alternatively, a multispecific antibody may be constructed by linking two or more types of binding proteins that bind to antigens on the surface of immune cells.

When such a bispecific (or multispecific) antibody is used, immune cells may recognize SARS-CoV-2 by antibody-dependent cellular cytotoxicity (ADCC) and induce neutralization of the virus.

When the stabilized Ace2 variant of the present invention is used, immune cells may effectively recognize and kill SARS-CoV-2 due to the high binding force between SARS-CoV-2 and Ace2, and when Ace2 is applied to therapeutic agents since it is structurally stable, it has excellent stability against storage and environmental changes, and may exhibit long-term drug effects even at a low dose by maintaining a structure effective for disease treatment in the human body for a long period of time. In addition, since the recognition site of the cell receptor in the antigen on the surface does not change even if a virus mutation occurs, it has the advantage of exhibiting a virus killing effect against various mutant strains.

Accordingly, the present invention relates to a pharmaceutical composition for preventing or treating SARS-CoV-2 virus infectious diseases, comprising the stabilized Ace2 variant or Ace2-Fc fusion protein.

The stabilized Ace2 variant of the present invention may strongly bind to SARS-CoV-2 because it comprises a protein derived from Ace2, which is a human cell receptor for SARS-CoV-2. Thus, it may interfere with the interaction between SARS-CoV-2 and the Ace2 receptor present in human cells. In addition, the Ace2-Fc fusion protein into which the stabilized Ace2 variant is introduced may effectively neutralize the SARS-CoV-2 virus through an immune response.

According to the experimental results described in the present inventor's prior Korean Patent Application No. 10-2021-0090947, it was confirmed that the SARS-CoV-2 spike protein-expressing lung cells could be killed by treating the wild-type Ace2-Fc fusion protein to lung cells transfected with the SARS-CoV-2 spike expression vector. In addition, it was confirmed that when the Ace2-Fc fusion protein was treated to the abdominal cavity of transgenic mice infected with the SARS-CoV-2 virus, the viral titer remarkably decreased compared to the control group.

Accordingly, it was confirmed through the research of the present inventor's prior patent application that the Ace2-Fc fusion protein exhibited a therapeutic effect on SARS-CoV-2 infectious diseases, and it was confirmed through the Experimental Examples described later of the present invention that when the stabilized Ace2 variant was used, the binding force of the wild-type Ace2 protein and the SARS-CoV-2 spike protein was similar and the stability was superior, and thus, it can be seen that the preventive or therapeutic effect of SARS-CoV-2 virus infectious diseases will be excellent when the stabilized Ace2 variant according to the present invention is used.

Thus, when the stabilized Ace2 variant or Ace2-Fc fusion protein of the present invention is used, there may be provided a pharmaceutical composition capable of preventing or treating coronavirus infectious disease 19 (COVID-19), which is SARS-CoV-2 virus infectious disease.

The pharmaceutical composition of the present invention may comprise a pharmaceutically acceptable carrier in addition to the stabilized Ace2 variant or the stabilized Ace2-Fc fusion protein.

The pharmaceutically acceptable carriers are those commonly used in formulations and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition of the present invention may further comprise a lubricant, a wetting agent, a sweetener, a flavoring agent, an emulsifier, a suspending agent, a preservative, and the like, in addition to the ingredients as described above.

The pharmaceutical composition of the present invention may be administered orally or parenterally, and for parenteral administration, it may be administered by intravenous injection, subcutaneous injection, intramuscular injection, intraperitoneal injection, endothelial administration, topical administration, intranasal administration, intrapulmonary administration, intrarectal administration, and the like.

The pharmaceutical composition of the present invention may be formulated in the form of a sterile injection solution, a lyophilized formulation, a pre-filled syringe solution, an oral formulation, an external preparation or a suppository, according to conventional methods. When administered orally, the oral composition may be formulated to coat the active agent or protect it from digestion in the stomach because the protein or peptide is digested.

The pharmaceutical composition of the present invention may further comprise at least one other therapeutic agent or diagnostic agent. For example, it may further comprise interferons, anti-S protein monoclonal antibodies, anti-S protein polyclonal antibodies, nucleoside analogs, DNA polymerase inhibitors, siRNA preparations or therapeutic vaccines as antiviral drugs.

SARS-CoV-2 infection and diseases caused by SARS-CoV-2 infection may be prevented or treated by administering the pharmaceutical composition of the present invention to mammals including humans. In this case, the dose depends on the subject to be treated, the severity of the disease or condition, the rate of administration and the judgment of the prescribing physician. For example, the daily dose of the stabilized Ace2-Fc fusion protein may be, for example, 0.01 μg/kg to 100 mg/kg.

The present invention also relates to a method of preventing or treating coronavirus infectious disease-19 (COVID-19), wherein the method may comprise administering a pharmaceutical composition comprising the stabilized Ace2-Fc fusion protein in an effective amount.

In the present invention, the subject to be administered may be a subject, specifically, a subject in need of administration of the Ace2-Fc fusion protein, and the subject may be an animal, usually a mammal, for example, a human.

EXAMPLES

Hereinafter, the present invention will be described in more detail through examples. However, these Examples show some experimental methods and compositions only for illustrating the present invention, and the scope of the present invention is not limited to these Examples.

Preparative Example 1: Preparation of Stabilized Ace2 Variants

Variants in which a disulfide bond was introduced into a residue pair causing instability in the Ace2 protein structure were designed and are shown in Table 1 below. In addition, C-alpha distances between amino acids and stabilization mechanisms in the amino acid residue pairs to be mutated are shown in Table 1 together.

TABLE 1

| No. | Ace 2 variation | Ace2 variant Sequence ID | C-alpha distance (Å) | Stabilization mechanism |
|---|---|---|---|---|
| 1 | N51C/V343C | SEQ ID NO: 3 | 5.3 | Stabilization of loop region at positions 331-347 |
| 2 | N53C/Q340C | SEQ ID NO: 4 | 5.9 | |
| 3 | I54C/K341C | SEQ ID NO: 5 | 6.0 | |
| 4 | H239C/V604C | SEQ ID NO: 6 | 6.1 | Stabilization of loop region at positions 599-614 |
| 5 | I21C/E87C | SEQ ID NO: 7 | 6.6 | Helix-helix stabilixation |
| 6 | M62C/S47C | SEQ ID NO: 8 | 4.8 | |
| 7 | A193C/V107C | SEQ ID NO: 9 | 6.5 | |

TABLE 1-continued

| No. | Ace 2 variation | Ace2 variant Sequence ID | C-alpha distance (Å) | Stabilization mechanism |
|---|---|---|---|---|
| 8 | V364C/V298C | SEQ ID NO: 10 | 6.6 | |
| 9 | T365C/T294C | SEQ ID NO: 11 | 4.8 | |
| 10 | H401C/H378C | SEQ ID NO: 12 | 5.7 | |
| 11 | T445C/T276C | SEQ ID NO: 13 | 5.2 | |
| 12 | S502C/R169C | SEQ ID NO: 14 | 6.2 | |
| 13 | N508C/S124C | SEQ ID NO: 15 | 5.6 | |
| 14 | A348C/H378C | SEQ ID NO: 16 | 6.3 | Strand-helix stabilization |

```
N51C/V343C
                                                                        [SEQ ID NO: 3]
MSSSSWLLLSLVAVTAAQSTIEEQAKTFLDKFNHEAEDLFYQSSLASWNYCTNITEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQKACCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

N53C/Q340C
                                                                        [SEQ ID NO: 4]
MSSSSWLLLSLVAVTAAQSTIEEQAKTFLDKFNHEAEDLFYQSSLASWNYNTCITEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVCKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

I54C/K341C
                                                                        [SEQ ID NO: 5]
MSSSSWLLLSLVAVTAAQSTIEEQAKTFLDKFNHEAEDLFYQSSLASWNYNTNCTEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQCAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

H239C/V604C
                                                                        [SEQ ID NO: 6]
MSSSSWLLLSLVAVTAAQSTIEEQAKTFLDKFNHEAEDLFYQSSLASWNYNTNITEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYECLHAY

VRAKLMNAYPSYISPIGCLPAHLLGDMWGRFWTNLYSLTVPFGQKPNIDVTDAMVDQAWDAQRIFKEAEKFFVSVGLPNMT
```

-continued

QGFWENSMLTDPGNVQKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFCGWSTDWSPYAD

I21C/E87C

[SEQ ID NO: 7]

MSSSSWLLLSLVAVTAAQSTCEEQAKTFLDKFNHEAEDLFYQSSLASWNYNTNITEENVQNMNNAGDKWSAFLKEQSTLAQ

MYPLQCIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

M62C/S47C

[SEQ ID NO: 8]

MSSSSWLLLSLVAVTAAQSTIEEQAKTFLDKFNHEAEDLFYQSSLACWNYNTNITEENVQNCNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

A193C/V107C

[SEQ ID NO: 9]

MSSSSWLLLSLVAVTAAQSTIEEQAKTFLDKFNHEAEDLFYQSSLASWNYNTNITEENVQNMNNAGDKWSAFLKEQSTLAQ

MYPLQEIQNLTVKLQLQALQQNGSSCLSEDKSKRLNTILNTMSTIYSTGKVCNPDNPQECLLLEPGLNEIMANSLDYNERL

WAWESWRSEVGKQLRPLYEEYVVLKNEMARCNHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

V364C/V298C

[SEQ ID NO: 10]

MSSSSWLLLSLVAVTAAQSTIEEQAKTFLDKFNHEAEDLFYQSSLASWNYNTNITEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMCDQAWDAQRIFKEAEKFFVSVGLPNMT

QGFWENSMLTDPGNVQKAVCHPTAWDLGKGDFRILMCTKCTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

T365C/T294C

-continued

[SEQ ID NO: 11]
MSSSSWLLLSLVAVTAAQSTIEEQAKTFLDKFNHEAEDLFYQSSLASWNYNTNITEENVQNMNNAGDKWSAFLKEQSTLAQ
MYPLQEIQNLTVKLQLQALQQNGSSVLSEDKSKRLNTILNTMSTIYSTGKVCNPDNPQECLLLEPGLNEIMANSLDYNERL
WAWESWRSEVGKQLRPLYEEYVVLKNEMARANHYEDYGDYWRGDYEVNGVDGYDYSRGQLIEDVEHTFEEIKPLYEHLHAY
VRAKLMNAYPSYISPIGCLPAHLLGDMWGRFWTNLYSLTVPFGQKPNIDVCDAMVDQAWDAQRIFKEAEKFFVSVGLPNMT
QGFWENSMLTDPGNVQKAVCHPTAWDLGKGDFRILMCTKVCMDDFLTAHHEMGHIQYDMAYAAQPFLLRNGANEGFHEAVG
EIMSLSAATPKHLKSIGLLSPDFQEDNETEINFLLKQALTIVGTLPFTYMLEKWRWMVFKGEIPKDQWMKKWWEMKREIVG
VVEPVPHDETYCDPASLFHVSNDYSFIRYYTRTLYQFQFQEALCQAAKHEGPLHKCDISNSTEAGQKLFNMLRLGKSEPWT
LALENVVGAKNMNVRPLLNYFEPLFTWLKDQNKNSFVGWSTDWSPYAD

H401C/H378C

[SEQ ID NO: 12]
MSSSSWLLLSLVAVTAAQSTIEEQAKTFLDKFNHEAEDLFYQSSLASWNYNTNITEENVQNMNNAGDKWSAFLKEQSTLAQ
MYPLQEIQNLTVKLQLQALQQNGSSVLSEDKSKRLNTILNTMSTIYSTGKVCNPDNPQECLLLEPGLNEIMANSLDYNERL
WAWESWRSEVGKQLRPLYEEYVVLKNEMARANHYEDYGDYWRGDYEVNGVDGYDYSRGQLIEDVEHTFEEIKPLYEHLHAY
VRAKLMNAYPSYISPIGCLPAHLLGDMWGRFWTNLYSLTVPFGQKPNIDVTDAMVDQAWDAQRIFKEAEKFFVSVGLPNMT
QGFWENSMLTDPGNVQKAVCHPTAWDLGKGDFRILMCTKVTMDDFLTAHHEMGCIQYDMAYAAQPFLLRNGANEGFCEAVG
EIMSLSAATPKHLKSIGLLSPDFQEDNETEINFLLKQALTIVGTLPFTYMLEKWRWMVFKGEIPKDQWMKKWWEMKREIVG
VVEPVPHDETYCDPASLFHVSNDYSFIRYYTRTLYQFQFQEALCQAAKHEGPLHKCDISNSTEAGQKLFNMLRLGKSEPWT
LALENVVGAKNMNVRPLLNYFEPLFTWLKDQNKNSFVGWSTDWSPYAD

T445C/T276C

[SEQ ID NO: 13]
MSSSSWLLLSLVAVTAAQSTIEEQAKTFLDKFNHEAEDLFYQSSLASWNYNTNITEENVQNMNNAGDKWSAFLKEQSTLAQ
MYPLQEIQNLTVKLQLQALQQNGSSVLSEDKSKRLNTILNTMSTIYSTGKVCNPDNPQECLLLEPGLNEIMANSLDYNERL
WAWESWRSEVGKQLRPLYEEYVVLKNEMARANHYEDYGDYWRGDYEVNGVDGYDYSRGQLIEDVEHTFEEIKPLYEHLHAY
VRAKLMNAYPSYISPIGCLPAHLLGDMWGRFWCNLYSLTVPFGQKPNIDVTDAMVDQAWDAQRIFKEAEKFFVSVGLPNMT
QGFWENSMLTDPGNVQKAVCHPTAWDLGKGDFRILMCTKVTMDDFLTAHHEMGHIQYDMAYAAQPFLLRNGANEGFHEAVG
EIMSLSAATPKHLKSIGLLSPDFQEDNETEINFLLKQALCIVGTLPFTYMLEKWRWMVFKGEIPKDQWMKKWWEMKREIVG
VVEPVPHDETYCDPASLFHVSNDYSFIRYYTRTLYQFQFQEALCQAAKHEGPLHKCDISNSTEAGQKLFNMLRLGKSEPWT
LALENVVGAKNMNVRPLLNYFEPLFTWLKDQNKNSFVGWSTDWSPYAD

S502C/R169C

[SEQ ID NO: 14]
MSSSSWLLLSLVAVTAAQSTIEEQAKTFLDKFNHEAEDLFYQSSLASWNYNTNITEENVQNMNNAGDKWSAFLKEQSTLAQ
MYPLQEIQNLTVKLQLQALQQNGSSVLSEDKSKRLNTILNTMSTIYSTGKVCNPDNPQECLLLEPGLNEIMANSLDYNERL
WAWESWCSEVGKQLRPLYEEYVVLKNEMARANHYEDYGDYWRGDYEVNGVDGYDYSRGQLIEDVEHTFEEIKPLYEHLHAY
VRAKLMNAYPSYISPIGCLPAHLLGDMWGRFWTNLYSLTVPFGQKPNIDVTDAMVDQAWDAQRIFKEAEKFFVSVGLPNMT
QGFWENSMLTDPGNVQKAVCHPTAWDLGKGDFRILMCTKVTMDDFLTAHHEMGHIQYDMAYAAQPFLLRNGANEGFHEAVG
EIMSLSAATPKHLKSIGLLSPDFQEDNETEINFLLKQALTIVGTLPFTYMLEKWRWMVFKGEIPKDQWMKKWWEMKREIVG
VVEPVPHDETYCDPACLFHVSNDYSFIRYYTRTLYQFQFQEALCQAAKHEGPLHKCDISNSTEAGQKLFNMLRLGKSEPWT
LALENVVGAKNMNVRPLLNYFEPLFTWLKDQNKNSFVGWSTDWSPYAD

N508C/S124C

[SEQ ID NO: 15]
MSSSSWLLLSLVAVTAAQSTIEEQAKTFLDKFNHEAEDLFYQSSLASWNYNTNITEENVQNMNNAGDKWSAFLKEQSTLAQ
MYPLQEIQNLTVKLQLQALQQNGSSVLSEDKSKRLNTILNTMCTIYSTGKVCNPDNPQECLLLEPGLNEIMANSLDYNERL
WAWESWRSEVGKQLRPLYEEYVVLKNEMARANHYEDYGDYWRGDYEVNGVDGYDYSRGQLIEDVEHTFEEIKPLYEHLHAY
VRAKLMNAYPSYISPIGCLPAHLLGDMWGRFWTNLYSLTVPFGQKPNIDVTDAMVDQAWDAQRIFKEAEKFFVSVGLPNMT

-continued

QGFWENSMLTDPGNVQKAVCHPTAWDLGKGDFRILMCTKVTMDDFLTAHHEMGHIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSCDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

A348C/H378C

[SEQ ID NO: 16]

MSSSSWLLLSLVAVTAAQSTIEEQAKTFLDKFNHEAEDLFYQSSLASWNYNTNITEENVQNMNNAGDKWSAFLKEQSTLAQ

MYPLQEIQNLTVKLQLQALQQNGSSVLSEDKSKRLNTILNTMSTIYSTGKVCNPDNPQECLLLEPGLNEIMANSLDYNERL

WAWESWRSEVGKQLRPLYEEYVVLKNEMARANHYEDYGDYWRGDYEVNGVDGYDYSRGQLIEDVEHTFEEIKPLYEHLHAY

VRAKLMNAYPSYISPIGCLPAHLLGDMWGRFWTNLYSLTVPFGQKPNIDVTDAMVDQAWDAQRIFKEAEKFFVSVGLPNMT

QGFWENSMLTDPGNVQKAVCHPTCWDLGKGDFRILMCTKVTMDDFLTAHHEMGCIQYDMAYAAQPFLLRNGANEGFHEAVG

EIMSLSAATPKHLKSIGLLSPDFQEDNETEINFLLKQALTIVGTLPFTYMLEKWRWMVFKGEIPKDQWMKKWWEMKREIVG

VVEPVPHDETYCDPASLFHVSNDYSFIRYYTRTLYQFQFQEALCQAAKHEGPLHKCDISNSTEAGQKLFNMLRLGKSEPWT

LALENVVGAKNMNVRPLLNYFEPLFTWLKDQNKNSFVGWSTDWSPYAD

FIGS. 2 and 3 show the positions of residue pairs to be mutated in the three-dimensional structure of Ace2 protein.

Figure 2A:
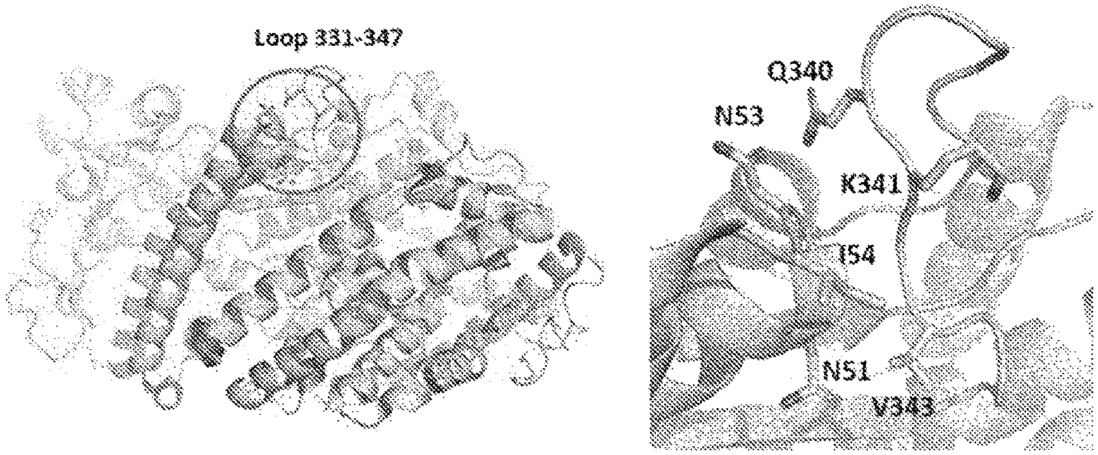
FIGS. 2A and 2B show the positions of residue pairs to be mutated for loop stabilization, specifically the positions of residue pairs N51/V343, N53/Q340 and I54/K341 for stabilization of loop 331-347 region (3A) and the position of residue pair H239/V604 for stabilization of loop 599-614 region (3B) according to an embodiment of the present invention in the three-dimensional structure of Ace2 protein.
Figure 2B:
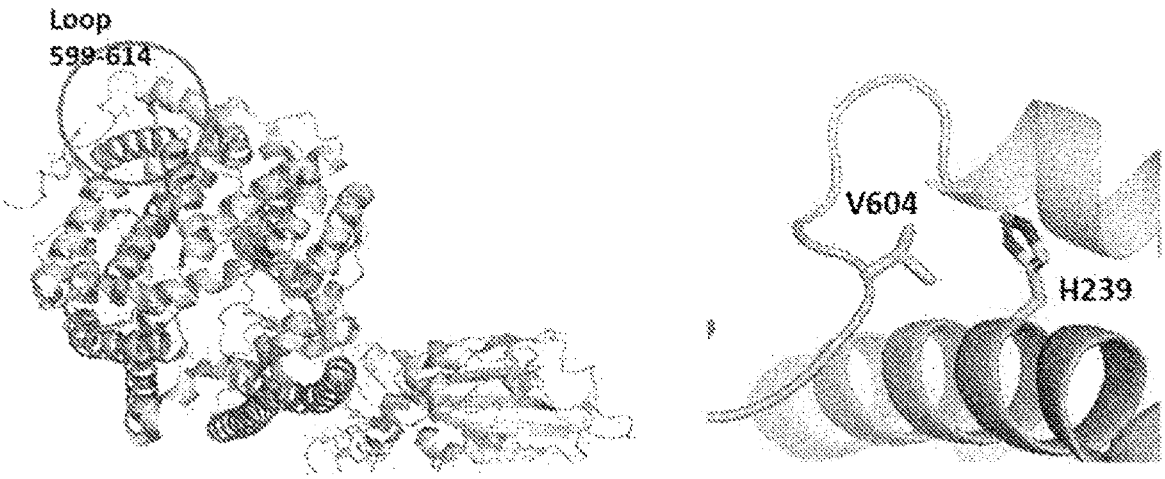
Figure 3A:
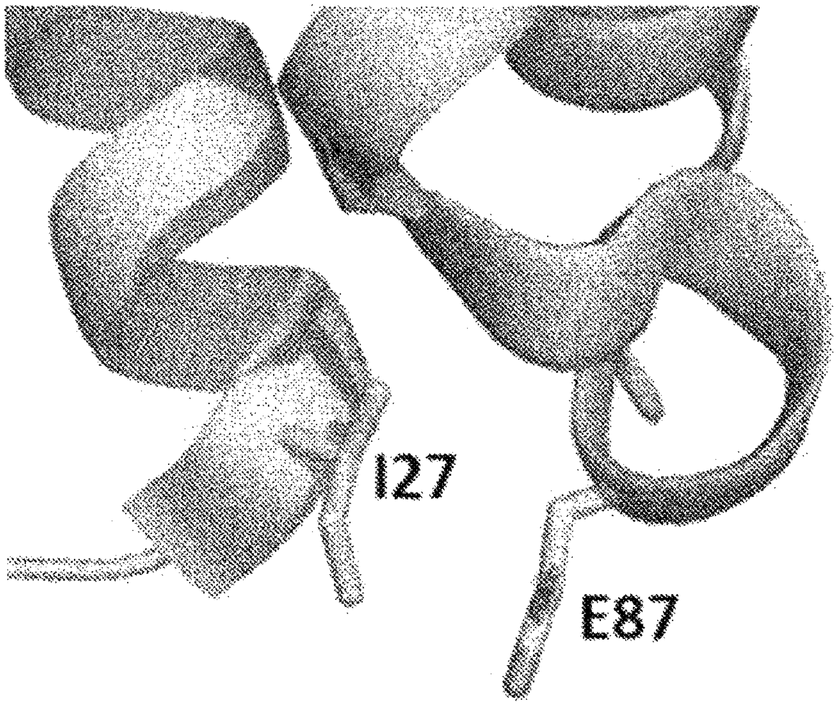
Figure 3B:
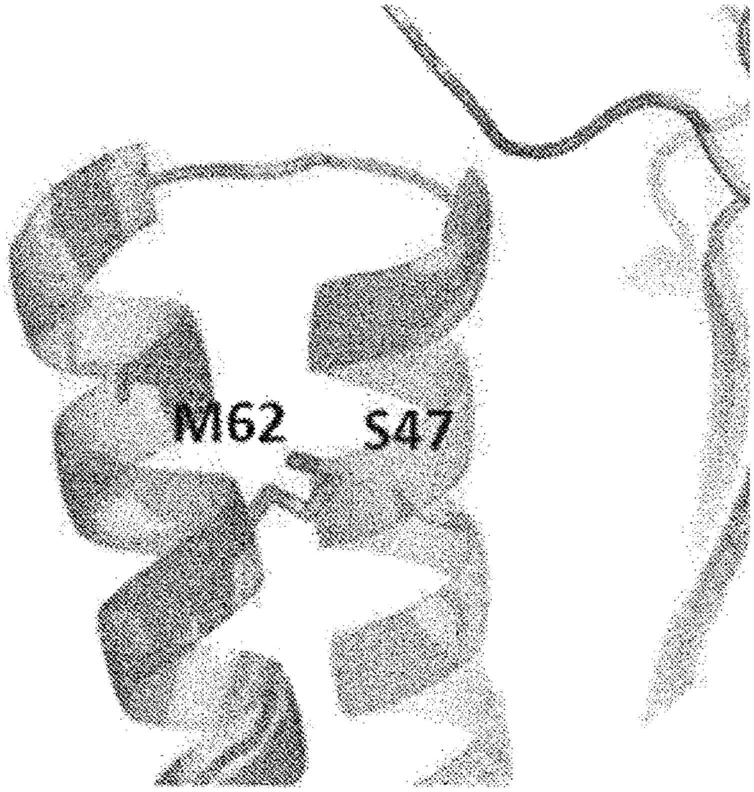
Figure 3C:
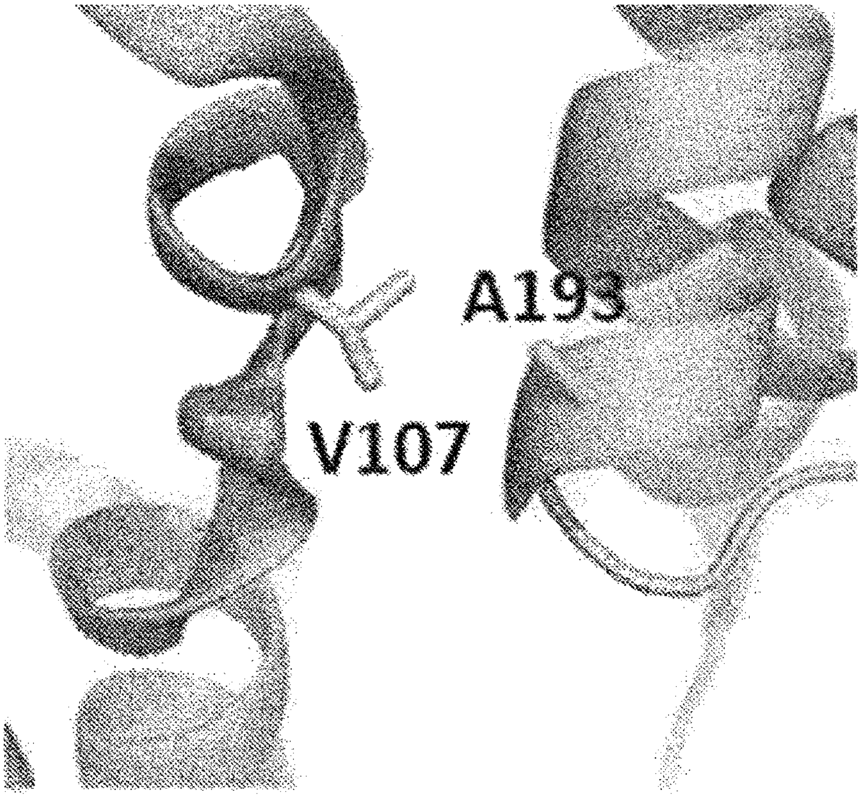
Figure 3D:
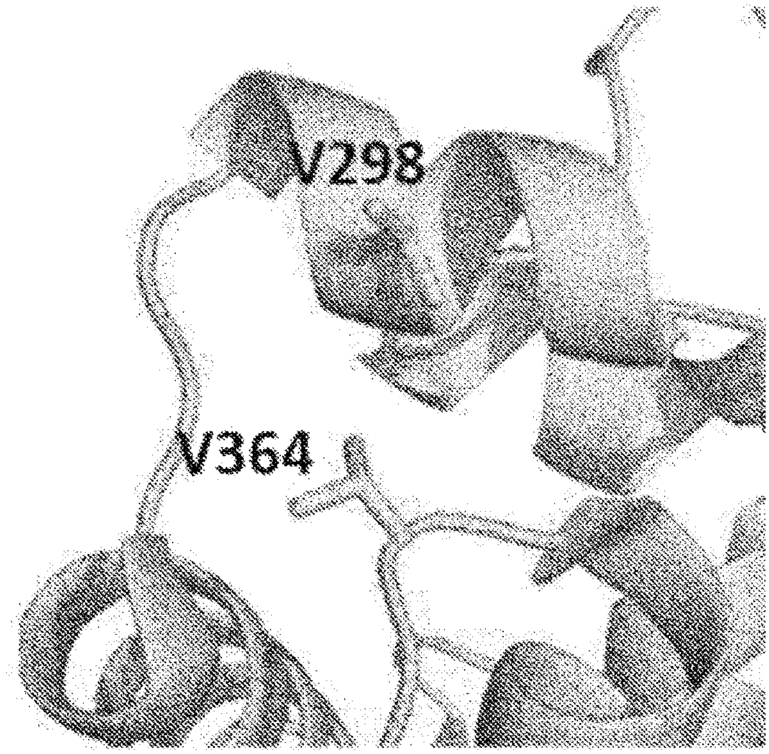
Figure 3E:
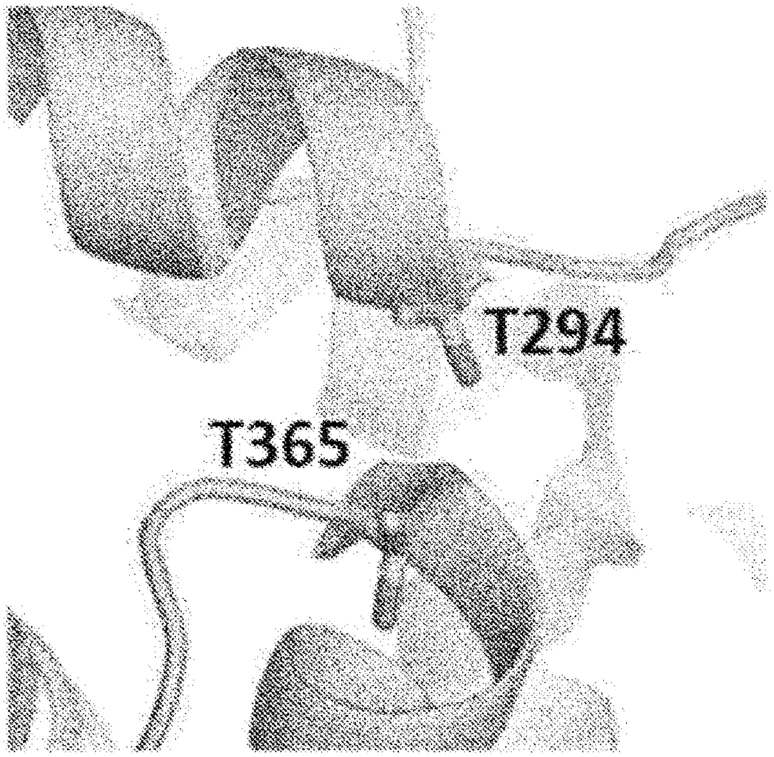
Figure 3F:
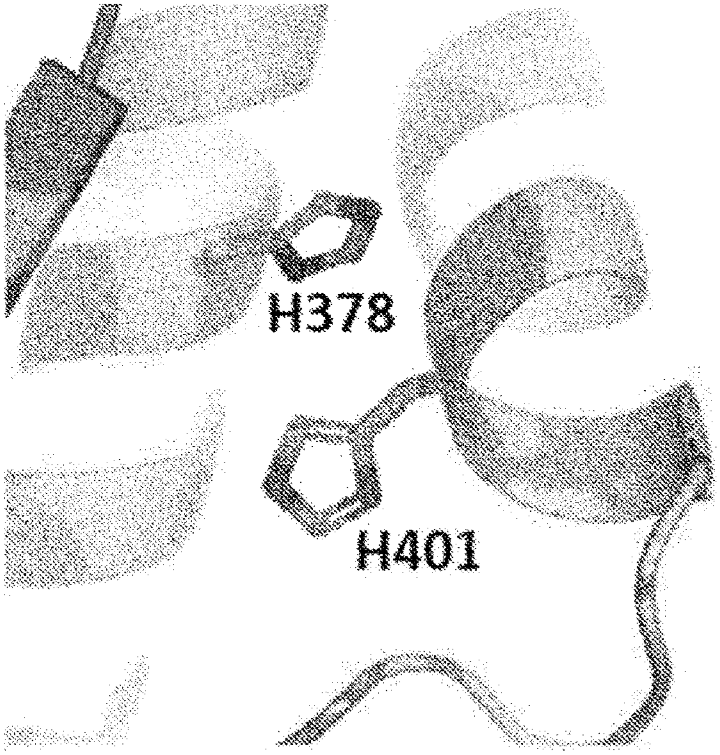
Figure 3G:
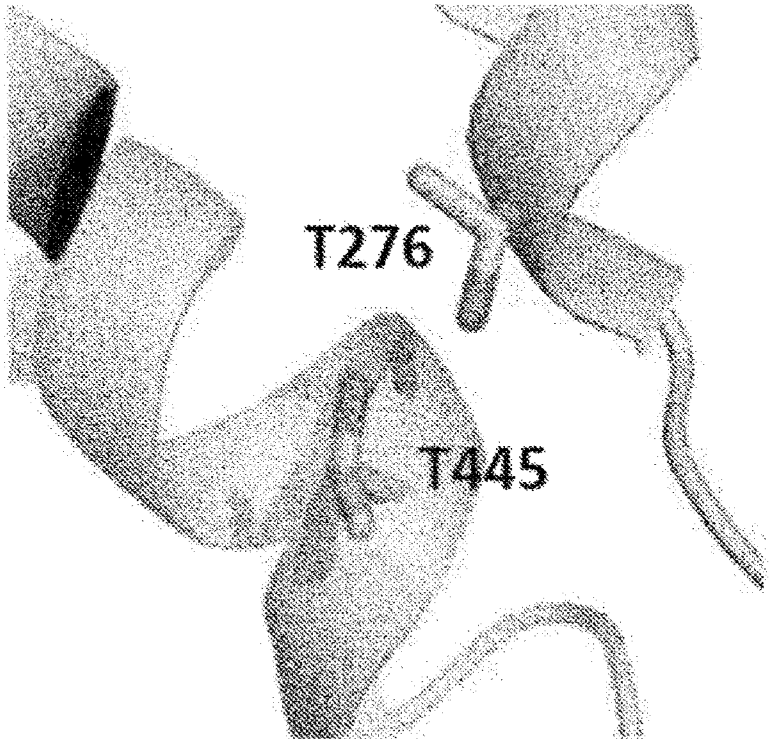
Figure 3H:
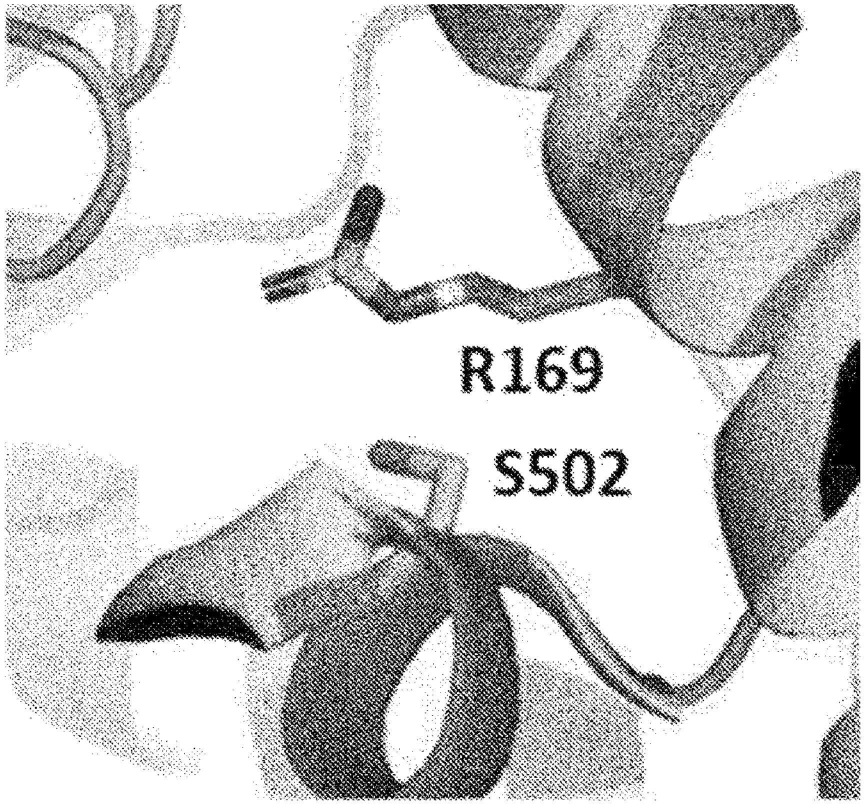
Figure 3I:
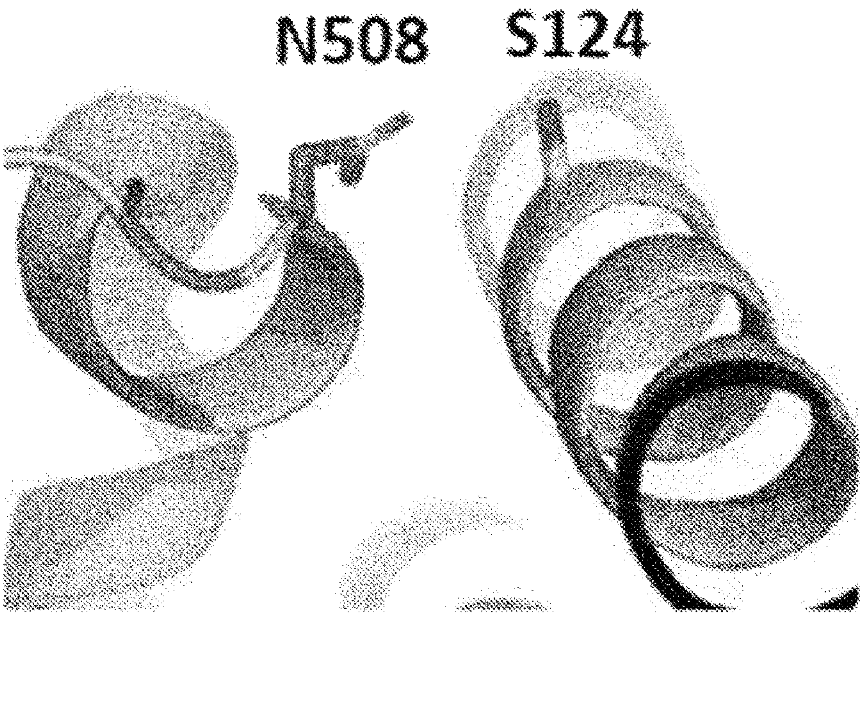

Specifically, FIGS. 2A and 2B show stabilized residues in the loop region of the Ace2 protein. In each image on the left of FIG. 2, the bold protein portion represents the Ace2 protein, and the light protein portion represents the spike protein of SARS-CoV-2.

As shown in FIG. 2A, N51/V343, N53/Q340 and 154/1 (341 were selected as residue pairs capable of stabilizing the loop region at positions 331-347 by introducing a disulfide bond, and as shown in FIG. 2B, H239/V604 was selected as a residue pair capable of stabilizing the loop region at positions 599-614. It was confirmed that the C-alpha distance between the residue pairs was a minimum of 5.2 Å and a maximum of 6.1 Å, which is within the range of 4.5 to 7.0 Å.

FIGS. 3A to 3I show stabilized residues in the helix-helix region of the Ace2 protein.

As shown in FIGS. 3A to 3I, I21/E87, M62/S47, A193/V107, V364/V298, T365/T294, H401/H378, T445/T276, S502/R169 and N508/S124 were selected as residue pairs capable of stabilizing the helix region by introducing a disulfide bond. It was confirmed that the C-alpha distance between the residue pairs was a minimum of 4.8 Å and a maximum of 6.6 Å, which is within the range of 4.5 to 7.0 Å.

FIG. 3J shows stabilized residues in the strand-helix region of the Ace2 protein.

As shown in FIG. 3J, A348/H378 was selected as a residue pair capable of stabilizing the strand-helix region by introducing a disulfide bond. It was confirmed that the C-alpha distance between the residue pairs was 6.3 Å, which is within the range of 4.5 to 7.0 Å.

Preparative Example 2: Preparation of Ace2-Fc Fusion Proteins

Based on the stabilized variants of the Ace2 proteins, Ace2-Fc fusion proteins were constructed.

2-1. Construction of Expression Vectors

An expression vector was constructed based on pcDNA 3.1/Myc His-A (Invitrogen).

DNA encoding the amino acid sequence of the target protein was amplified by polymerase chain reaction, and then was cloned using restriction enzyme and T4 DNA ligase. Through this, it was expressed with a human immunoglobulin G1 (IgG1) Fc tag and a histidine tag at the C-terminal end of residues at positions 1 to 615 of the Ace2 protein.

Primers were constructed according to the Quik Change Site-directed mutagenesis (Stratagene) protocol, and mutations were introduced through polymerase chain reaction. After the treatment, it was confirmed that the intended sequence change was made to all nucleotides using a DNA sequencing service.

FIGS. 4A to 4N show amino acid sequences encoded by the stabilized Ace2-Fc expression vector into which mutations 1 to 14 in Preparative Example were introduced (see Table 2 below). In FIG. 4, the part underlined with a straight line corresponds to the Ace2-derived protein region, and the part underlined with a dotted line corresponds to IgG1 221-447 region in the Fc domain. Residues substituted with cysteine in wild-type Ace2 are marked with asterisks, and linkers and tags are not separately marked.

TABLE 2

| FIG. | Ace 2 variation | Protein Sequence |
|---|---|---|
| 4A | N51C/V343C | SEQ ID NO: 3 (Ace2 mutant)-GSGSGS (linker)-SEQ ID NO: 2 (Fc region)-GTHHHHHH (tag) |
| 4B | N53C/Q340C | SEQ ID NO: 4 (Ace2 mutant)-GSGSGS (linker)-SEQ ID NO: 2 (Fc region)-GTHHHHHH (tag) |
| 4C | I54C/K341C | SEQ ID NO: 5 (Ace2 mutant)-GSGSGS (linker)-SEQ ID NO: 2 (Fc region)-GTHHHHHH (tag) |

TABLE 2-continued

| FIG. | Ace 2 variation | Protein Sequence |
|---|---|---|
| 4D | H239C/V604C | SEQ ID NO: 6 (Ace2 mutant)-GSGSGS (linker)-SEQ ID NO: 2 (Fc region)-GTHHHHHH (tag) |
| 4E | I21C/E87C | SEQ ID NO: 7 (Ace2 mutant)-GSGSGS (linker)-SEQ ID NO: 2 (Fc region)-GTHHHHHH (tag) |
| 4F | M62C/S47C | SEQ ID NO: 8 (Ace2 mutant)-GSGSGS (linker)-SEQ ID NO: 2 (Fc region)-GTHHHHHH (tag) |
| 4G | A193C/V107C | SEQ ID NO: 9 (Ace2 mutant)-GSGSGS (linker)-SEQ ID NO: 2 (Fc region)-GTHHHHHH (tag) |
| 4H | V364C/V298C | SEQ ID NO: 10 (Ace2 mutant)-GSGSGS (linker)-SEQ ID NO: 2 (Fc region)-GTHHHHHH (tag) |
| 4I | T365C/T294C | SEQ ID NO: 11 (Ace2 mutant)-GSGSGS (linker)-SEQ ID NO: 2 (Fc region)-GTHHHHHH (tag) |
| 4J | H401C/H378C | SEQ ID NO: 12 (Ace2 mutant)-GSGSGS (linker)-SEQ ID NO: 2 (Fc region)-GTHHHHHH (tag) |
| 4K | T445C/T276C | SEQ ID NO: 13 (Ace2 mutant)-GSGSGS (linker)-SEQ ID NO: 2 (Fc region)-GTHHHHHH (tag) |
| 4L | S502C/R169C | SEQ ID NO: 14 (Ace2 mutant)-GSGSGS (linker)-SEQ ID NO: 2 (Fc region)-GTHHHHHH (tag) |
| 4M | N508C/S124C | SEQ ID NO: 15 (Ace2 mutant)-GSGSGS (linker)-SEQ ID NO: 2 (Fc region)-GTHHHHHH (tag) |
| 4N | A348C/H378C | SEQ ID NO: 16 (Ace2 mutant)-GSGSGS (linker)-SEQ ID NO: 2 (Fc region)-GTHHHHHH (tag) |

2-2. Protein Expression

Expression vectors were transfected into ExpiCHO™ cells to transiently express each protein.

In transfection, the cells were diluted to a concentration of $6\times10^{6}$ cells/mL, and mixed with the expression vector so that the final concentration of the expression vector was 0.8 μg DNA/mL. ExpiCHO™ Expression Medium, OptiPRO™ SFM and ExpiFectamine™ transfection kit (Gibco) were used in this process according to the manufacturer's instructions.

The transfected cells were cultured in a carbon dioxide incubator under 8% carbon dioxide conditions for 8 days, and then the supernatant containing the recombinant protein was separated by centrifugation.

2-3. Purification

In order to separate target proteins from the culture broth containing each recombinant protein, affinity chromatography was performed using a Ni-NTA (Qiagen) column.

Specifically, the Ni-NTA column was filled with a buffer solution containing 50 mM Tris-HCl, pH 7.5 and 200 mM NaCl, and then, the culture broth obtained through centrifugation was filtered through 0.45 μm filter paper and introduced. The reaction with the culture broth was completed, and then, the column was washed sequentially with a buffer solution containing 50 mM Tris-HCl, pH 7.5 and 500 mM NaCl, and a buffer solution containing 50 mM Tris-HCl, pH 7.5, 200 mM NaCl and 30 mM imidazole. Finally, proteins bound to the column were eluted using a buffer solution containing 50 mM Tris-HCl, pH 7.5, 200 mM NaCl, and 500 mM imidazole. After elution, the composition of the buffer solution containing the protein was replaced with a composition containing 20 mM Tris-HCl, pH 7.5 and 150 mM NaCl using a Hitrap™ Desalting (GE healthcare) column.

Experimental Example 1: Measurement of Protein Stability Through Thermal Shift Assay In order to measure the stability of the protein, thermal shift assay was performed using Protein Thermal Shift™ Dye Kit (Thermo Fisher Scientific).

The fluorescent dye stock solution and protein were diluted in a buffer solution so that the final composition of the mixed solution was 0.1 M HEPES, pH 7.5, 150 mM NaCl, and then mixed. The concentration of protein was adjusted so that the final concentration was 0.5 mg/ml. 20 μl of the mixed solution was dispensed into MicroAmp Optical 8-Tube Strip (Thermo Fisher Scientific). For real-time fluorescence measurement, an Applied Biosystems 7500 Real-Time PCR System (Thermo Fisher Scientific) instrument was used, and a melting curve was obtained using a melting curve protocol inputted into the software.

The first derivative melting curve of the stabilized Ace2 (N51C/V343C)-Fc protein through the thermal shift assay is shown in FIG. 5, and for comparison, the same assay was performed on the wild-type Ace2(WT)-Fc protein and shown together. In FIG. 5, the melting curve of the stabilized Ace2(N51C/V343C)-Fc protein is marked as a dashed line, and the melting curve of the wild-type Ace2(WT)-Fc protein is marked as a straight line. In addition, the melting temperature of the protein was calculated through the above curve and is shown in Table 3.

TABLE 3

| Ace2 Protein | Tm (° C.) |
|---|---|
| Wild-type Ace2-Fc | 53.9 |
| S47C/M62C | 55.4 |
| N51C/V343C | 58.8 |
| N53C/Q340C | 56.6 |
| I54C/K341C | 61.2 |

As can be seen in FIG. 5 and Table 3, it was confirmed that the melting temperature of the protein using the stabilized Ace2 having S47C/M62C, N51C/V343C, N53C/Q340C or I54C/K341C variation was 55.4° C., 58.8° C., 56.6° C. and 61.2° C., respectively, which were more than 1° C. higher than the melting temperature of the wild type, 53.9° C. In particular, the melting temperature of N51C/V343C variation was about 5° C. higher than that of the wild type, and the melting temperature of I54C/K341C variation was increased by 7° C. or more compared with the wild type. Through such excellent thermal stability results, it was confirmed that the stabilized Ace2 variant of the present invention was structurally very stable compared to the wild type.

Experimental Example 2: Measurement of Binding Force to SARS-CoV-2 Spike Protein Through Enzyme-Linked Immunosorbent Assay (ELISA)

The SARS-CoV-2 spike protein (residues 319-541) was diluted to a concentration of 2.5 μg/ml in a buffer solution having a composition of 0.1 M sodium carbohydrate, pH 9.0, and coated on a 96-well plate.

After coating, the plate was blocked using 5% (w/v) skim milk powder. Ace2(N51C/V343C)-Fc protein and wild-type Ace2(WT)-Fc protein diluted in 5% (w/v) skim milk powder at each concentration were added to each coated well, and then reacted at room temperature for 2 hours.

The reaction-completed solution was discarded, and an HRP-binding secondary antibody (GW Vitek) capable of binding to human Fc antibody diluted in 5% (w/v) skim milk powder was added and reacted at room temperature for 2 hours. At the end of each process, the wells were washed three times with phosphate buffer solution.

Figure 6:
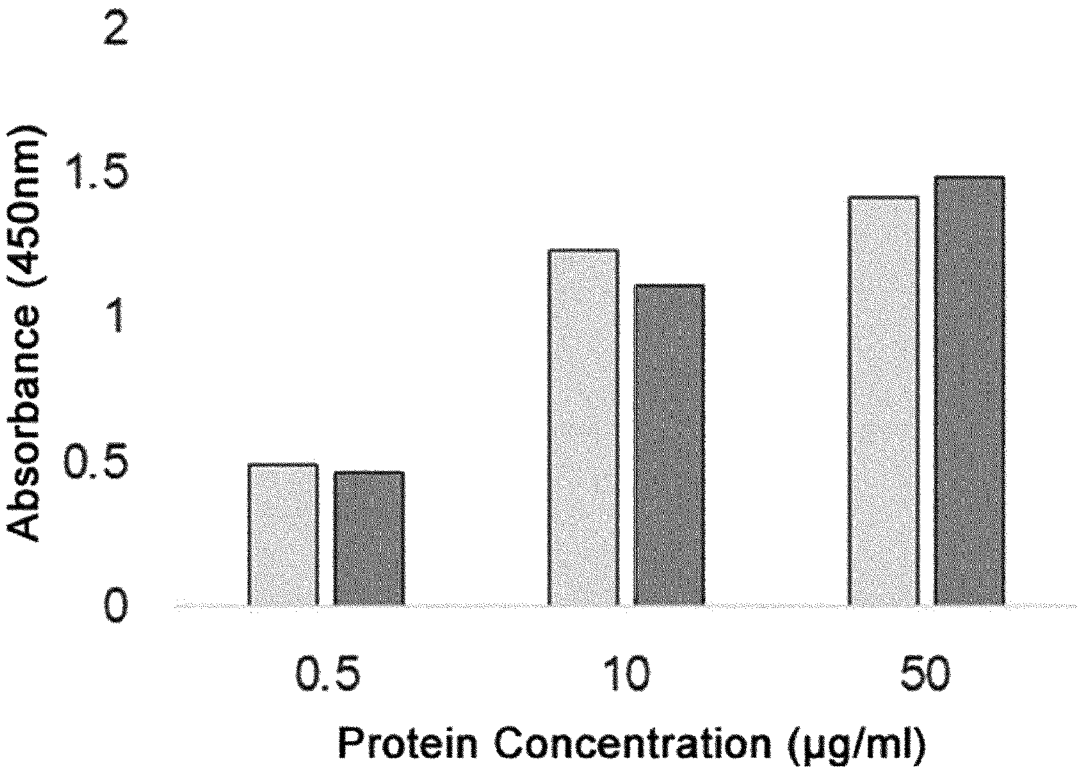
FIG. 6 shows ELISA analysis results of the stabilized Ace2-Fc fusion protein according to an embodiment of the present invention and a wild-type Ace2-Fc fusion protein.

After the reaction was completed, tetramethylbenzidine (KOMA Biotech) solution was put into each well, left to develop color, and then 0.2 M sulfuric acid solution was added to stop the reaction. The absorbance of the reaction-completed solution was measured at 450 nm, and the results are shown in FIG. 6. In FIG. 6, at each concentration, the left bar shows the result for the wild-type Ace2(WT)-Fc protein, and the right bar shows the result for the stabilized Ace2 (N51C/V343C)-Fc protein.

According to the results of FIG. 6, it was confirmed that the protein into which the stabilized Ace2 according to the present invention was introduced had a binding force to the SARS-CoV-2 spike protein very similar to that of the protein into which wild type Ace2 was introduced.

Accordingly, it could be confirmed that the stabilized Ace2 variant of the present invention may effectively improve only the stability of the Ace2 protein without significantly affecting the binding force with the SARS-CoV-2 spike protein.

As a specific part of the present invention has been described in detail above, it will be apparent to those skilled in the art that these specific descriptions are only preferred embodiments, and the scope of the present invention is not limited thereby. Accordingly, it is intended that the substantial scope of the present invention be defined by the appended claims and equivalents thereof.

What is claimed is:

1. A stabilized angiotensin-converting enzyme 2 (Ace2) variant comprising a disulfide bond formed by substituting cysteine for one or more of the amino acid residue pairs present in an Ace2-derived protein, wherein the Ace2-derived protein comprises the amino acid sequence of SEQ ID NO: 1, and wherein the amino acid residue pair comprises one or more selected from the group consisting of N51 and V343, N53 and Q340, 154 and K341, and M62 and S47.

2. The stabilized Ace2 variant according to claim 1, wherein the distance between the central carbons (C-alphas) in the amino acid residue pairs forming the disulfide bond is from 4.5 to 7.0 Å.

3. An Ace2-Fc fusion protein comprising the stabilized Ace2 variant according to claim 1 linked to one or two chains of an immunoglobulin (Ig) Fc domain.

4. The Ace2-Fc fusion protein according to claim 3, wherein the stabilized Ace2 variant and the Fc domain are linked through a linker consisting of 0 to 20 amino acid residues.

5. The Ace2-Fc fusion protein according to claim 3, wherein the Ace2-Fc fusion protein is a homodimer or a heterodimer.

6. The Ace2-Fc fusion protein according to claim 3, wherein the immunoglobulin is IgG1, IgG2, IgG3, or IgG4.

7. The Ace2-Fc fusion protein according to claim 3, wherein the one or two chains of the Fc domain comprise amino acid residues at positions 221 to 447 (based on EU numbering) in the heavy chain of an IgG1.

8. A method for or treating coronavirus infectious disease 19 (COVID-19), comprising the step of administering to a subject in need thereof a composition comprising the Ace2-Fc fusion protein of claim 3.

* * * * *

SEQUENCE LISTING

```
Sequence total quantity: 16
SEQ ID NO: 1           moltype = AA  length = 615
FEATURE                Location/Qualifiers
source                 1..615
                       mol_type = protein
                       organism = synthetic construct
SEQUENCE: 1
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 2           moltype = AA  length = 227
FEATURE                Location/Qualifiers
source                 1..227
                       mol_type = protein
                       organism = synthetic construct
SEQUENCE: 2
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 3           moltype = AA  length = 615
FEATURE                Location/Qualifiers
source                 1..615
                       mol_type = protein
                       organism = synthetic construct
SEQUENCE: 3
MSSSSWLLLS LVAVTAAQST IEEQAKTFLD KFNHEAEDLF YQSSLASWNY CTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
```

-continued

HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVQ KACCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYAD 615

SEQ ID NO: 4 moltype = AA length = 615
FEATURE Location/Qualifiers
source 1..615
mol_type = protein
organism = synthetic construct
SEQUENCE: 4
MSSSSWLLLS LVAVTAAQST IEEQAKTFLD KFNHEAEDLF YQSSLASWNY NTCITEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVC KAVCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYAD 615

SEQ ID NO: 5 moltype = AA length = 615
FEATURE Location/Qualifiers
source 1..615
mol_type = protein
organism = synthetic construct
SEQUENCE: 5
MSSSSWLLLS LVAVTAAQST IEEQAKTFLD KFNHEAEDLF YQSSLASWNY NTNCTEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVQ CAVCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYAD 615

SEQ ID NO: 6 moltype = AA length = 615
FEATURE Location/Qualifiers
source 1..615
mol_type = protein
organism = synthetic construct
SEQUENCE: 6
MSSSSWLLLS LVAVTAAQST IEEQAKTFLD KFNHEAEDLF YQSSLASWNY NTNITEENVQ 60
NMNNAGDKWS AFLKEQSTLA QMYPLQEIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYECL 240
HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVQ KAVCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFCGWSTDW SPYAD 615

SEQ ID NO: 7 moltype = AA length = 615
FEATURE Location/Qualifiers
source 1..615
mol_type = protein
organism = synthetic construct
SEQUENCE: 7
MSSSSWLLLS LVAVTAAQST CEEQAKTFLD KFNHEAEDLF YQSSLASWNY NTNITEENVQ 60
NMNNAGDKWS AFLKEQSTLA QMYPLQCIQN LTVKLQLQAL QQNGSSVLSE DKSKRLNTIL 120
NTMSTIYSTG KVCNPDNPQE CLLLEPGLNE IMANSLDYNE RLWAWESWRS EVGKQLRPLY 180
EEYVVLKNEM ARANHYEDYG DYWRGDYEVN GVDGYDYSRG QLIEDVEHTF EEIKPLYEHL 240
HAYVRAKLMN AYPSYISPIG CLPAHLLGDM WGRFWTNLYS LTVPFGQKPN IDVTDAMVDQ 300
AWDAQRIFKE AEKFFVSVGL PNMTQGFWEN SMLTDPGNVQ KAVCHPTAWD LGKGDFRILM 360
CTKVTMDDFL TAHHEMGHIQ YDMAYAAQPF LLRNGANEGF HEAVGEIMSL SAATPKHLKS 420
IGLLSPDFQE DNETEINFLL KQALTIVGTL PFTYMLEKWR WMVFKGEIPK DQWMKKWWEM 480
KREIVGVVEP VPHDETYCDP ASLFHVSNDY SFIRYYTRTL YQFQFQEALC QAAKHEGPLH 540
KCDISNSTEA GQKLFNMLRL GKSEPWTLAL ENVVGAKNMN VRPLLNYFEP LFTWLKDQNK 600
NSFVGWSTDW SPYAD 615

```
SEQ ID NO: 8           moltype = AA  length = 615
FEATURE                Location/Qualifiers
source                 1..615
                       mol_type = protein
                       organism = synthetic construct
SEQUENCE: 8
MSSSSWLLLS LVAVTAAQST IEEQAKTFLD KFNHEAEDLF YQSSLACWNY NTNITEENVQ  60
NCNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 9           moltype = AA  length = 615
FEATURE                Location/Qualifiers
source                 1..615
                       mol_type = protein
                       organism = synthetic construct
SEQUENCE: 9
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSCLSE DKSKRLNTIL  120
NTMSTIYSTG KVCNPDNPQE CLLLEPGLNE IMANSLDYNE RLWAWESWRS EVGKQLRPLY  180
EEYVVLKNEM ARCNHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 10          moltype = AA  length = 615
FEATURE                Location/Qualifiers
source                 1..615
                       mol_type = protein
                       organism = synthetic construct
SEQUENCE: 10
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMCDQ  300
AWDAQRIFKE AEKFFVSVGL PNMTQGFWEN SMLTDPGNVQ KAVCHPTAWD LGKGDFRILM  360
CTKCTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 11          moltype = AA  length = 615
FEATURE                Location/Qualifiers
source                 1..615
                       mol_type = protein
                       organism = synthetic construct
SEQUENCE: 11
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVCDAMVDQ  300
AWDAQRIFKE AEKFFVSVGL PNMTQGFWEN SMLTDPGNVQ KAVCHPTAWD LGKGDFRILM  360
CTKVCMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 12          moltype = AA  length = 615
FEATURE                Location/Qualifiers
source                 1..615
                       mol_type = protein
                       organism = synthetic construct
SEQUENCE: 12
```

-continued

```
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGCIQ YDMAYAAQPF LLRNGANEGF CEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                   615

SEQ ID NO: 13           moltype = AA  length = 615
FEATURE                 Location/Qualifiers
source                  1..615
                        mol_type = protein
                        organism = synthetic construct
SEQUENCE: 13
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWCNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALCIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                   615

SEQ ID NO: 14           moltype = AA  length = 615
FEATURE                 Location/Qualifiers
source                  1..615
                        mol_type = protein
                        organism = synthetic construct
SEQUENCE: 14
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWCS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ACLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                   615

SEQ ID NO: 15           moltype = AA  length = 615
FEATURE                 Location/Qualifiers
source                  1..615
                        mol_type = protein
                        organism = synthetic construct
SEQUENCE: 15
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMCTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSCDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                   615

SEQ ID NO: 16           moltype = AA  length = 615
FEATURE                 Location/Qualifiers
source                  1..615
                        mol_type = protein
                        organism = synthetic construct
SEQUENCE: 16
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTCWD LGKGDFRILM  360
CTKVTMDDFL TAHHEMGCIQ YDMAYAAQPF LLRNGANEGF HEAVGEIMSL SAATPKHLKS  420
```

-continued

| | |
|---|---|
| IGLLSPDFQE DNETEINFLL KQALTIVGTL PFTYMLEKWR WMVFKGEIPK DQWMKKWWEM | 480 |
| KREIVGVVEP VPHDETYCDP ASLFHVSNDY SFIRYYTRTL YQFQFQEALC QAAKHEGPLH | 540 |
| KCDISNSTEA GQKLFNMLRL GKSEPWTLAL ENVVGAKNMN VRPLLNYFEP LFTWLKDQNK | 600 |
| NSFVGWSTDW SPYAD | 615 |